(12) United States Patent
Khait et al.

(10) Patent No.: US 9,107,604 B2
(45) Date of Patent: Aug. 18, 2015

(54) SYSTEMS AND METHODS FOR GENERATING ELECTROMAGNETIC INTERFERENCE FREE LOCALIZATION DATA FOR AN IN-VIVO DEVICE

(71) Applicant: GIVEN IMAGING LTD., Yoqneam (IL)

(72) Inventors: Semion Khait, Tiberias (IL); Oren Rosenberg, Kiryat Ono (IL)

(73) Assignee: GIVEN IMAGING LTD., Yoqneam (IL)

( * ) Notice: Subject to any disclaimer, the term of this patent is extended or adjusted under 35 U.S.C. 154(b) by 518 days.

(21) Appl. No.: 13/626,046

(22) Filed: Sep. 25, 2012

(65) Prior Publication Data

US 2013/0080119 A1  Mar. 28, 2013

Related U.S. Application Data

(60) Provisional application No. 61/539,183, filed on Sep. 26, 2011.

(51) Int. Cl.
| | |
|---|---|
| *H03F 1/26* | (2006.01) |
| *A61B 5/06* | (2006.01) |
| *A61B 5/00* | (2006.01) |
| *A61B 5/07* | (2006.01) |
| *A61B 1/04* | (2006.01) |

(52) U.S. Cl.
CPC ............... *A61B 5/065* (2013.01); *A61B 5/073* (2013.01); *A61B 5/7203* (2013.01); *A61B 1/041* (2013.01)

(58) Field of Classification Search
CPC .................... H04N 5/32; H04N 5/3577
USPC .................. 702/194, 195, 182–183, 185, 189
See application file for complete search history.

(56) References Cited

U.S. PATENT DOCUMENTS

| | | | |
|---|---|---|---|
| 4,278,077 A | 7/1981 | Mizumoto | |
| 5,604,531 A | 2/1997 | Iddan et al. | |
| 5,993,378 A | 11/1999 | Lemelson | |
| 6,240,312 B1 | 5/2001 | Alfano et al. | |
| 6,428,469 B1 | 8/2002 | Iddan et al. | |

(Continued)

FOREIGN PATENT DOCUMENTS

| | | |
|---|---|---|
| DE | 344 0177 | 5/1986 |
| JP | 04-109927 | 4/1992 |

(Continued)

*Primary Examiner* — Edward Raymond
(74) *Attorney, Agent, or Firm* — Pearl Cohen Zedek Latzer Baratz LLP

(57) ABSTRACT

An electromagnetic localization signal may be sensed by an electromagnetic field sensor in an in-vivo device with an electromagnetic field interference that is superimposed on the electromagnetic localization signal. The electromagnetic field interference may be filtered by outputting, by the electromagnetic field sensor, an alternating signal that represents, or in response to, the electromagnetic localization signal; sampling a first (e.g., positive) portion of the alternating signal during a first sampling window or period to obtain a first set of samples, sampling a second (e.g., negative) portion of the alternating signal during a second sampling window or period to obtain a second set of samples; and calculating a number, $N_R$, from the first and second sets of samples, that approximately represents a substantially interference free electromagnetic localization signal.

19 Claims, 21 Drawing Sheets

(56) References Cited

U.S. PATENT DOCUMENTS

| | | |
|---|---|---|
| 6,764,440 B2 | 7/2004 | Iddan et al. |
| 6,904,308 B2 | 6/2005 | Frisch et al. |
| 6,944,316 B2 | 9/2005 | Glukhovsky et al. |
| 7,009,634 B2 | 3/2006 | Iddan et al. |
| 7,778,356 B2 | 8/2010 | Bettesh |
| 2002/0103417 A1 | 8/2002 | Gazdzinski |
| 2006/0183993 A1 | 8/2006 | Horn |
| 2008/0193139 A1 | 8/2008 | Bettesh |
| 2008/0208077 A1 | 8/2008 | Iddan et al. |
| 2009/0290686 A1 * | 11/2009 | Liu et al. .................. 378/162 |

FOREIGN PATENT DOCUMENTS

| | | |
|---|---|---|
| JP | 1992-144533 | 5/1992 |
| WO | WO 2012/127469 | 9/2012 |

* cited by examiner

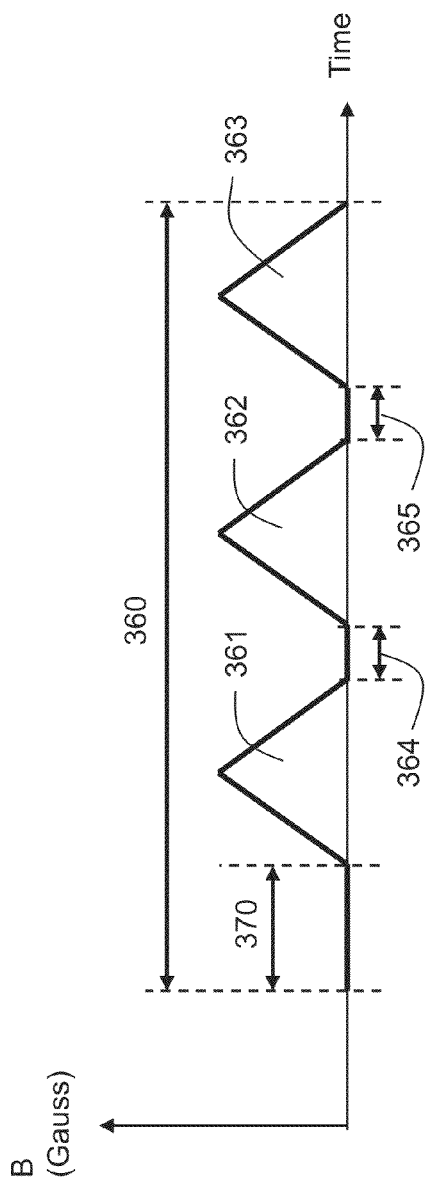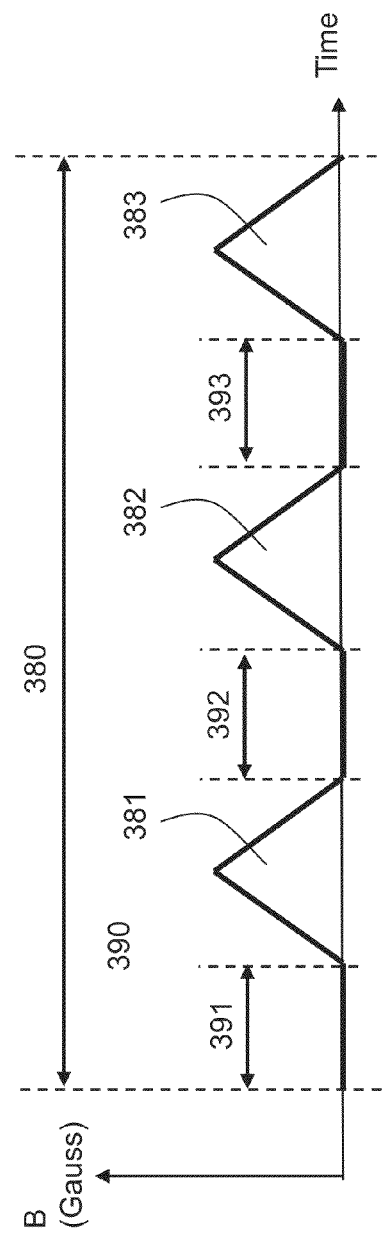

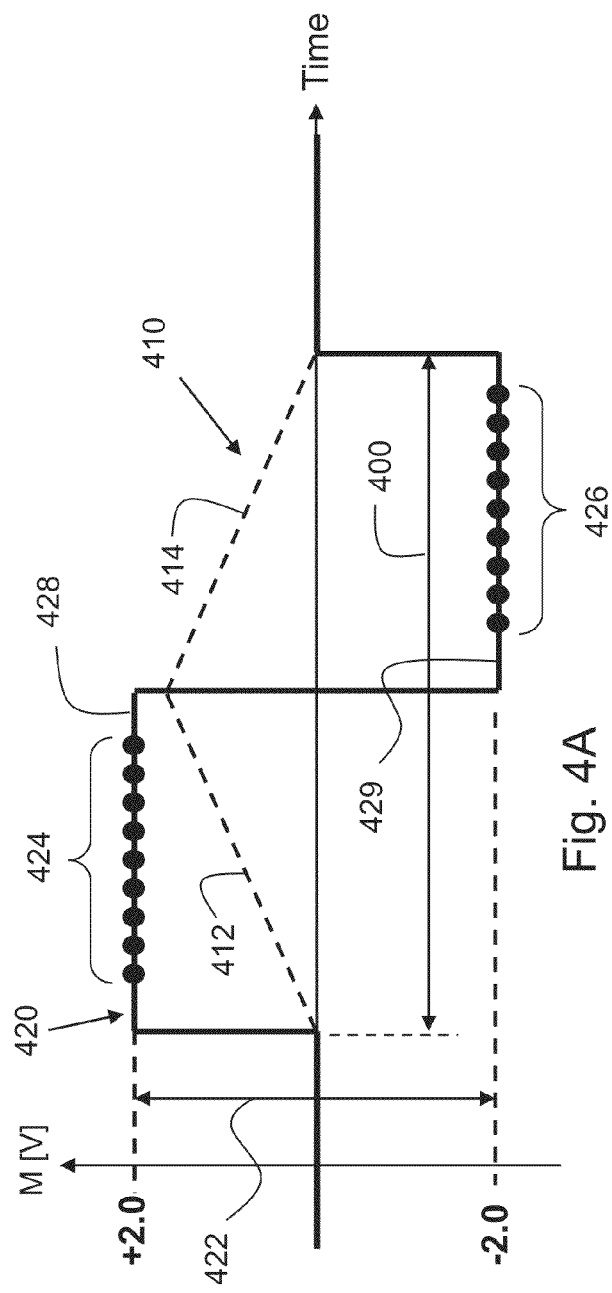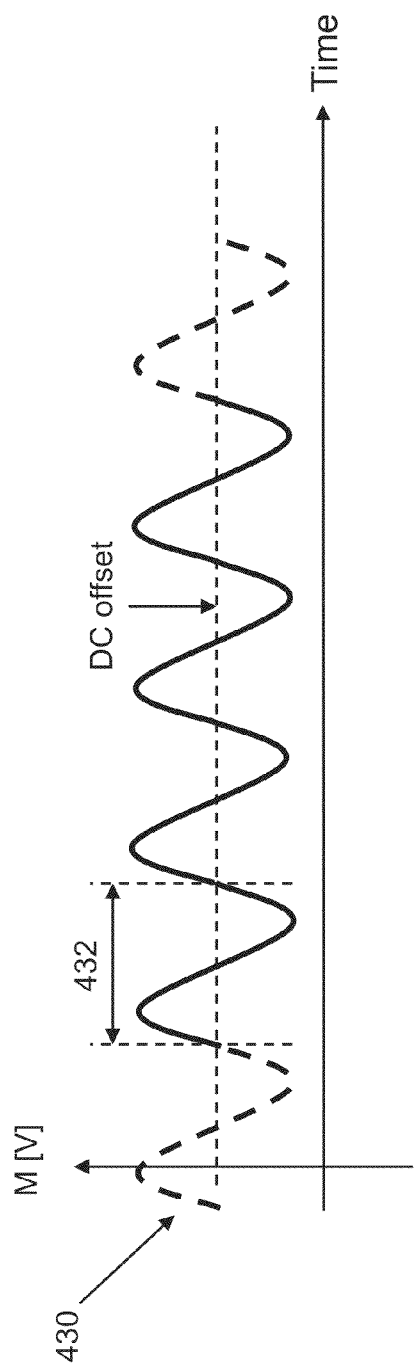
Fig. 4A
Fig. 4B

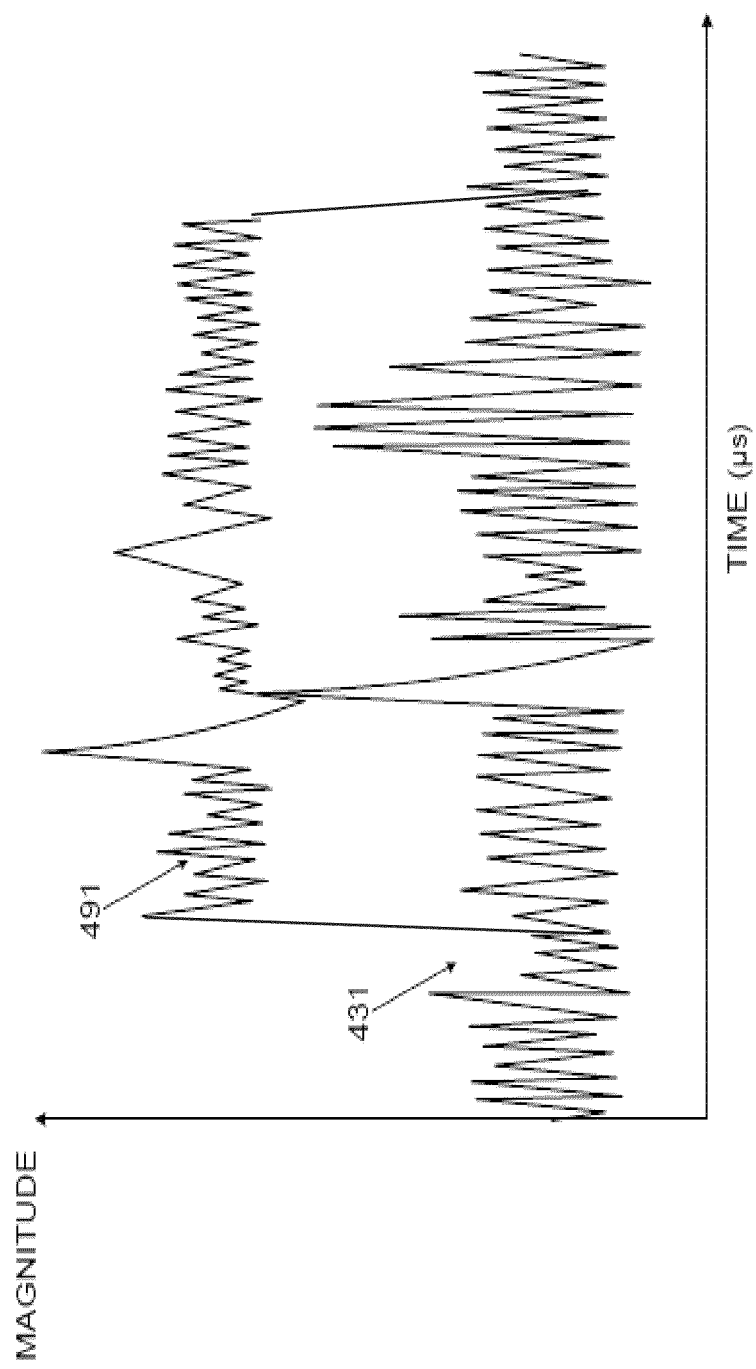

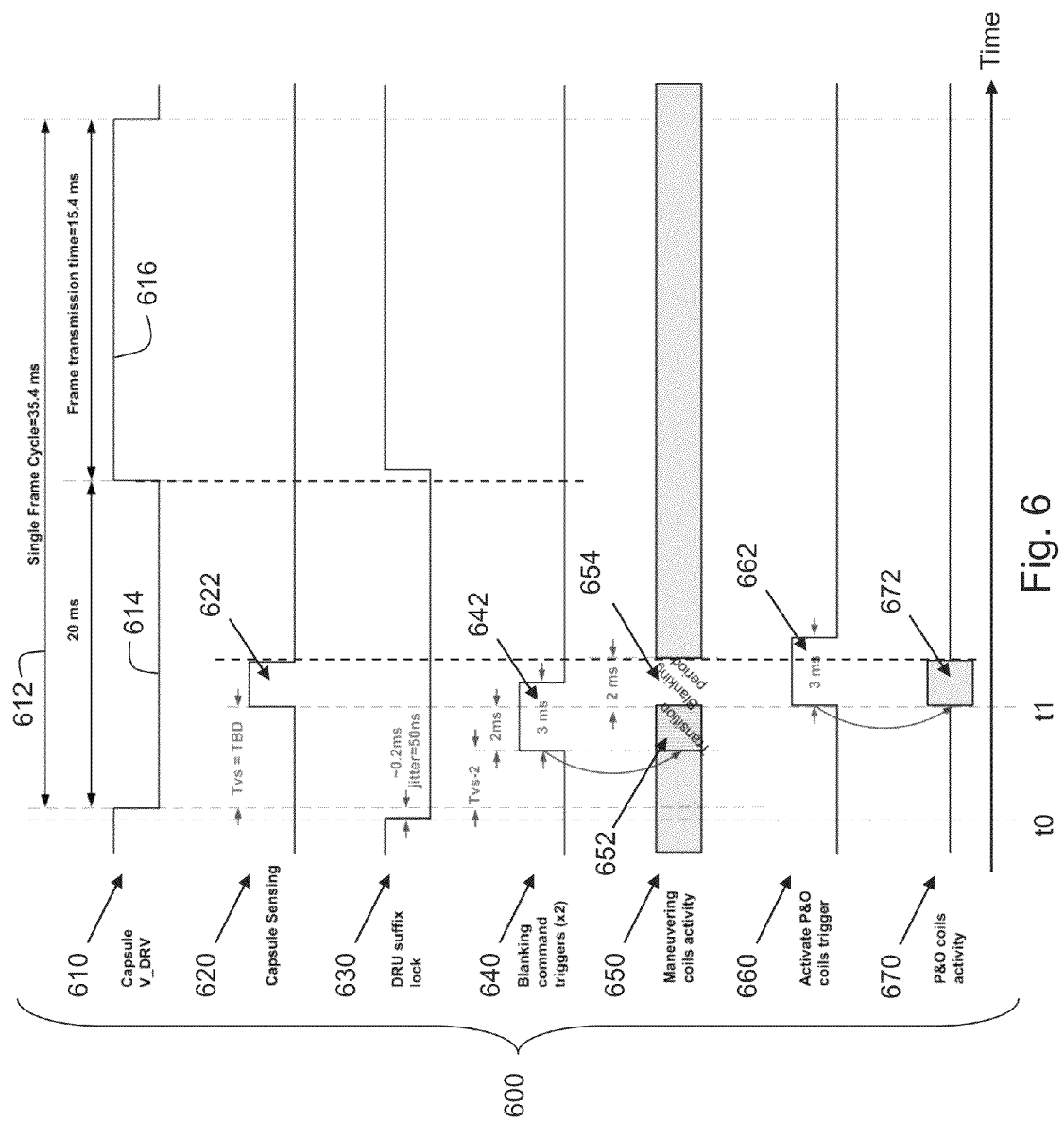

SYSTEMS AND METHODS FOR GENERATING ELECTROMAGNETIC INTERFERENCE FREE LOCALIZATION DATA FOR AN IN-VIVO DEVICE

PRIOR APPLICATION DATA

The present application claims benefit from prior provisional application No. 61/539,183, filed on Sep. 26, 2011, entitled "SYSTEMS AND METHODS FOR GENERATING ELECTROMAGNETIC INTERFERENCE FREE LOCALIZATION DATA FOR AN IN-VIVO DEVICE", incorporated herein by reference in its entirety.

FIELD OF THE INVENTION

The present invention generally relates to an in-vivo localization system and more specifically to methods for cancelling out electromagnetic interferences in localization signals, and to an in-vivo localization system using the electromagnetic interferences cancelling out methods.

BACKGROUND

In-vivo measuring systems are known in the art. Some in-vivo devices/systems that traverse the gastrointestinal (GI) system may include one or more imaging sensors, for imaging (e.g., capturing images of) the interior of the GI system, and/or sensors of other types. In-vivo devices may traverse the GI system by being pushed through the GI system by peristaltic force exerted by the digestive system, or by being maneuvered (e.g., magnetically). Some applications require knowing the current location and/or current orientation of the involved in-vivo device. For example, in order to magnetically maneuver an in-vivo device, for example in the GI system, the magnetic maneuvering system has to know the current location/orientation (and the target location/orientation) of the in-vivo device in order to generate the correct steering magnetic fields. Therefore, a localization system is also used to provide localization information to the magnetic maneuvering system, based on which the magnetic maneuvering system can maneuver the in-vivo device. A localization system may generate an alternating current ("AC") electromagnetic field that may be sensed by electromagnetic field sensors that are mounted in the in-vivo device. The location and/or orientation of the in-vivo device may be derived from the AC signals that the electromagnetic field sensors output.

An advanced maneuvering system may use an AC electromagnetic field and a direct current ("DC") electromagnetic field to maneuver devices in vivo. Operating an electromagnetic based localization system and an electromagnetic based maneuvering system at the same time results in mutual interference between the two systems. For example, an external maneuvering AC magnetic field generated by the maneuvering system may have a negative side effect on the readout of the localization electromagnetic field sensors of the in-vivo device, and the external AC localization signal generated by the localization system may have a negative side effect on the maneuvering force that maneuvers the in-vivo device. Therefore, it is preferable that the two systems operate intermittently, with one system (e.g., the maneuvering system) operated while the other system (e.g., electromagnetic based localization system) is temporarily disabled, and vice versa. However, due to the high currents that are required to generate maneuvering electromagnetic fields, the electromagnetic field, which may be generated by using a switching technique, may not be able to be shut down completely in time in, and for, the required time (e.g., when the localization sensing takes place). Inability to shut down the maneuvering electromagnetic field completely may result in a residual electromagnetic field that results in erroneous determination of the location of the in-vivo device.

Therefore, it would be beneficial to have methods that would enable a magnetic maneuvering system to steer an in-vivo device, and a magnetic localization system to locate the in-vivo device without the maneuvering system interfering with the operation of the localization system. While using the maneuvering field is beneficial, in general, from the maneuvering system's standpoint, it would be beneficial to have a (localization) system that can cancel out, or significantly reduce, the electromagnetic interference caused by such residual maneuvering fields.

SUMMARY

An electromagnetic localization signal burst may be sensed by electromagnetic field sensors in an in-vivo device with electromagnetic field interference that is superimposed on the electromagnetic localization signal burst. The signal burst may include n electromagnetic localization signals, where each electromagnetic localization signal may have a time duration $T_L$.

A method for filtering the interference from a noisy localization signal sensed by an in-vivo device may include performing, for each electromagnetic localization signal, cancelling out zero-order electromagnetic field interference and first-order electromagnetic field interference superimposed on the electromagnetic localization signal by outputting, by each electromagnetic field sensor, an alternating signal that represents the electromagnetic localization signal, sampling a positive portion of the alternating signal during a positive sampling window (e.g., a period of time) to obtain a first set of samples, sampling a negative portion of the alternating signal during a negative sampling window to obtain a second set of samples; and calculating or creating a number, $N_R$, from the first and second sets of samples, that approximately represents the alternating signal (and, therefore, the localization signal represented by the alternating signal). The term "alternating signal" may refer to any alternating signal for example whose shape is, or is substantially, square, or that generally resembles a square, and that has a discernible positive portion or a portion that is mostly positive, and a discernible negative portion or a portion that is mostly negative. A "positive sampling window" may be a sampling window during which a positive portion of the alternating square signal may be sampled (to obtain "positive samples"), and a "negative sampling window" may be a sampling window during which a negative portion of the alternating square signal may be sampled (to obtain "negative samples").

The electromagnetic field interference may include aperiodic and periodic electromagnetic field interferences of a zero-order, first-order, . . . , $n^{th}$-order, and the interference signal may include a fundamental frequency $f_I$ that satisfies the condition $2T_I < T_L$, where $T_I = 1/f_I$. The method may further include the steps of calculating a first number, Np, by adding up the first set of sample values; calculating a second number, Nn, by adding up the second set of sample values; calculating a third number, $N_R$, by subtracting the second number Nn from the first number Np, the third number $N_R$ representing a localization signal corresponding to the pertinent alternating signal; and repeating the steps for every alternating signal in the localization signal burst.

The method may further include sampling the interference during one or more quiet periods in the localization signal burst and modifying the number $N_R$ based on the sampling result, where sampling the interference during a quiet period may include sampling the interference during a first sampling window and a second sampling window to respectively obtain a third set of samples and a fourth set of samples; calculating a third number by adding up the third set of samples, and a fourth number by adding up the fourth set of samples; and, based on the third and the forth sets of samples, calculating a number NI1 that represents the interference signal during the quiet period.

The method may include monitoring the electromagnetic field interference signal to detect changes in the fundamental frequency of the interference, and adjusting sampling parameters to accommodate for changes in Ti.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures:

FIGS. 3A, 3B and 3C illustrate localization signal bursts according to an embodiment of the invention;

FIG. 4A illustrates a localization electromagnetic field and a resulting EMF localization signal induced in an in-vivo device according to an embodiment of the invention;

FIG. 4B illustrates an exemplary electromagnetic interference according to an embodiment of the invention;

FIGS. 4F and 4G respectively depict an oscilloscope image and a graphical illustration thereof of an example electromagnetic interference caused by a maneuvering electromagnetic field, and a noisy localization signal according to an embodiment of the invention;

FIG. 6 schematically illustrates a timing diagram according to an embodiment of the invention;

DETAILED DESCRIPTION

Figure 1:
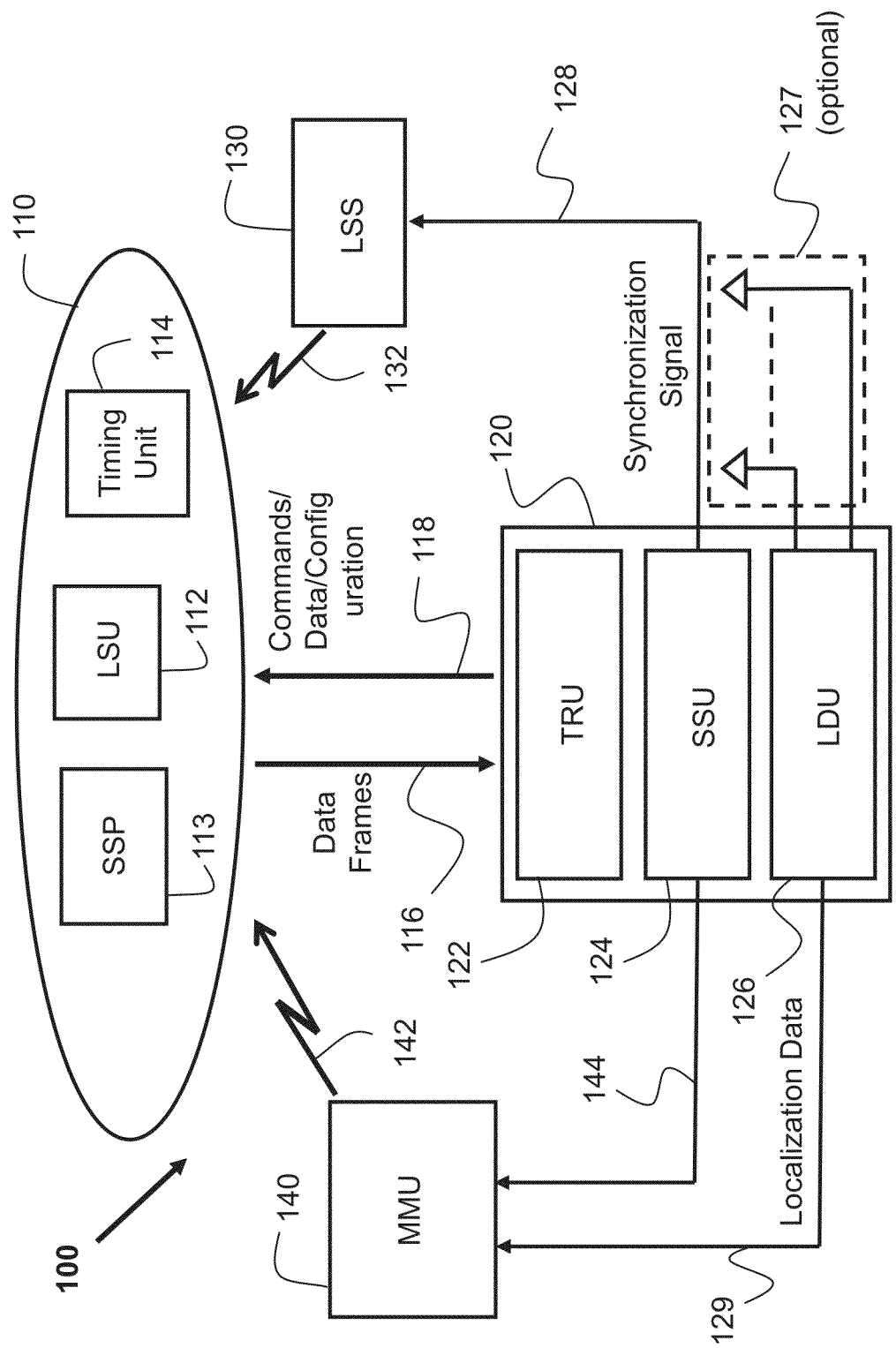
FIG. 1 is a block diagram of a localization and maneuvering system for localizing and maneuvering an in-vivo device according to an embodiment of the invention.

The description that follows provides various details of exemplary embodiments. However, this description is not intended to limit the scope of the claims but instead to explain various principles of the invention and the manner of practicing it.

Although embodiments of the invention are not limited in this regard, discussions utilizing terms such as, for example, "processing," "computing," "calculating," "determining," "inferring", "deducing", "establishing", "analyzing", "checking", or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information non-transitory storage medium that may store instructions to perform operations and/or processes. Unless explicitly stated, the method embodiments described herein are not constrained to a particular order or sequence of steps, operations or procedures. Additionally, some of the described method embodiments or elements thereof can occur or be performed at the same point in time.

An electromagnetic field sensing time window ("sensing window" for short) may be a period of time allocated in a work cycle of an in-vivo device for sensing electromagnetic localization signals, and possibly for processing the sensed signals. The in-vivo device may operate according to the work cycle. A "work cycle" may be a cycle or repeated time period, divided into time slots or periods, that includes a transmission period during which the in-vivo device transmits data (e.g., data frame; e.g., image frame, metadata, etc.), for example to a receiver or to a data recorder, via a first communication channel, and an idle period which is a period during which the in-vivo device does not transmit data via the first communication channel (but it may transmit data via a second, separate, communication channel or be occupied executing internal tasks). Time specifics (e.g., specific start time, specific duration, specific termination time, specific relative temporal position, etc.) that may define the sensing window or period may be defined such that the sensing window is temporally wide enough (e.g., of long enough duration) to enable the in-vivo device to sense as many electromagnetic localization signals as required to determine the location and/or orientation of the in-vivo device, and narrow enough and located in the work cycle such that it would not interfere with other activities that the in-vivo device may be performing or involved in. ('Time specifics' are specific time values of time parameters, where the sensing window/period's 'start time', 'duration', and so on, are example time parameters.) In one embodiment, using localization signals may facilitate determination of the location of the in-vivo device in, or using, for example, the X,Y,Z coordinates system, or the polar coordinates system. "Localization signal" and "orientation signal" are hereinafter collectively referred to herein as "localization signal" and "sensing signal". "Orientation" when used herein may include yaw, pitch and roll, or other components to determine for example the direction a device faces in three-dimensions. The term "localization signal" may refer to a signal such as a signal that represents a localization electromagnetic field/signal generated by a localization signals source ("LSS") external to the in-vivo device and sensed by the in-vivo device, and to the signal that an electromagnetic field sensor of the in-vivo device outputs in response to it. Therefore, the term "localization signal" should be construed contextually.

In general, an in-vivo device operating with an in-vivo device localization system may be capable, among other things, of: (i) transferring data frames to (and in some embodiments exchanging data with) the data recorder with which it operates, (ii) sensing localization signals (e.g., electromagnetic localization fields/signals, or, synonymously, localization electromagnetic fields/signals) that are generated by an external system, and (iii) processing the localization signals and transmitting corresponding localization data to the data recorder. The localization data that the in-vivo device may transmit may represent the raw localization signal(s) that each electromagnetic field sensor in the in-vivo device outputs, in which case the (raw) localization data may have to be processed by an external system in order to deduce or infer therefrom the location and/or orientation of the in-vivo device. Alternatively, the raw signals may be processed internally (by the in-vivo device), and the consequent localization data transmitted by or from the in-vivo device may represent the location (and/or orientation) of the in-vivo device. The data recorder may be capable, among other things, of: (i) receiving the data frames from the in-vivo device, (ii) using data frames to generate a synchronization signal in order to synchronize, for example, between the LSS generating the localization signals, the in-vivo device that senses the localization signals, and a magnetic maneuvering unit ("MMU") that may use localization data as feedback to maneuver the in-vivo device magnetically, and (iii) processing localization data, wholly or partly.

In one embodiment the system generating the localization signal may transmit localization signals at specific times and for specific time periods which are preset for (and governed by) the in-vivo device internal clock because localization signals are to be transmitted to the in-vivo device only during time slots or 'sensing windows' or time periods that the in-vivo device allocates or reserves for sensing this type of signals during work cycles. This type of synchronization helps ensure that localization signals are transmitted to the in-vivo device in each work cycle, or in selected work cycles, only when the in-vivo device is ready to receive and process them. The time specifics (e.g., timing and width or duration) of the sensing window may be predetermined or chosen in advance after taking into account various time constraints of the in-vivo device, such as a need to allocate a time slot for sensing a physical parameter in vivo (e.g., for imaging objects, sensing pH, etc.), another time slot for receiving instructions and/or data from an external source, another time slot for processing the instructions and/or data received from the external localization signals source, etc.

A timing mechanism in the in-vivo device, which may predominate the timing of various processes, tasks, etc. of the in-vivo device, may measure time (e.g., by counting clock pulses) in order to identify a start time (Ts) and a termination time (Tt) of each sensing window. During a sensing window, e.g., during the time period of the window, the in-vivo device may switch to or enter, and temporarily remain in, a sensing mode. During the sensing mode, the in-vivo device may sense a series of localization signals (e.g., in the form of localization signal bursts) during, for example, the respective sensing windows. When the sensing window elapses, the in-vivo device may exit the sensing mode, for example to start/commence or resume other tasks. Assuming a 3-dimensional location of the in-vivo device is determined by using the X,Y,Z coordinates system, a localization signal associated with the X-axis may be generated by an external system and sensed internally by the in-vivo device during a sensing window which is allocated for it, and other localization signals may likewise be generated and sensed for the Y-axis and for the Z-axis.

The external LSS that generates the localization signals may be subjected to various constraints with regard to the timing of the generation of the localization signals. For example, generating the localization signals while the in-vivo device is transmitting data (e.g., image data) may detrimentally affect the transmission and/or the reception of the data by a receiver (e.g., data recorder). Therefore, it may be beneficial to generate the localization signals while the in-vivo device is not transmitting data. However, as discussed above, since during idle periods the in-vivo device may still be busy doing other internal activities (e.g., receiving data, processing data), a synchronization signal is transferred to the LSS to thereby indicate to the LSS the sensing window that the in-vivo device has allocated for sensing localization signals. The synchronization signal may be produced externally to the in-vivo device (e.g., by the data recorder) based on the in-vivo device's restored timing mechanism (e.g., restored or generated reference time and restored master clock signal). Synchronizing between the in-vivo device and the LSS, therefore, means that the LSS generates the localization signals during a sensing window whose time specifics have been suited to, or governed or dictated by, the in-vivo device.

The way the in-vivo device's timing mechanism is restored by the data recorder (for example) and the way the consequent synchronization signal is used by the LSS are described below. Clock pulses originating from a master clock of the in-vivo device may be used to count time units (a time 'unit' may equal to, e.g., 1 microsecond) relative to a reference time. Any synchronization bit or group of bits that is/are contained in a data frame (e.g., prefix data, suffix data, etc.) that is transmitted by the in-vivo device may be used by a receiver (e.g., data recorder) to restore the clock pulses originating from the in-vivo device. Prefix data or suffix data, or both data, have the same relative location within each working cycle ((they do not change from frame to frame). Therefore, such data may be used to obtain synchronization. The restored clock pulses may be used by the receiver to count time by using the same time units and relative to the same reference time. Based on the time counting, the LSS may start transmitting a localization signal when the time count has a first value; e.g., Count1, and terminate the transmission when the time count has a second value, e.g., Count2 (where Count2>Count1). The in-vivo device may enter, transition to, or enable a sensing mode when the time count equals, for example, count value Count1, and exit or disable the sensing mode when the time count equals, for example, count value Count2. During the sensing mode, the in-vivo device may, during the time periods of the sensing window(s), sense and may process localization signal(s).

The magnetic maneuvering unit (MMU) may use an electromagnetic field to maneuver devices in vivo. Due to the high currents that are required to generate the maneuvering electromagnetic field, the electromagnetic field may be generated by using a switching technique such as the pulse width modulation ("PWM") switching technique. Due to the high currents and high switching frequency involved in using such a technique, the maneuvering system may not be able to be shut down completely when the localization system operates. Instead, the intensity of the electromagnetic field is decreased and 'locked' so as to 'freeze' the in-vivo device in space (e.g., retain the device at the same position and orientation) while the maneuvering system is shut down. Despite the maneuvering electromagnetic field decreased intensity, aperiodic and periodic interferences, which typically have a fundamental frequency and higher harmonies, are still superimposed on the localization signals and result in erroneous localization determination. However, by selecting a specific switching frequency and a certain type of localization signal, and employing a certain sampling scheme on the localization signal, most of the influential interferences may be cancelled out easily and efficiently, as described below, without requiring robust and lengthy filtering processes or extensive computation resources.

FIG. 1 is a block diagram of localization and maneuvering system 100 for localizing and maneuvering an in-vivo device according to an example embodiment. Maneuvering system 100, which is configured to maneuver an in-vivo device 110 (to which a data recorder 120 is functionally coupled), may include a localization signals source (LSS) 130 and a magnetic maneuvering unit (MMU) 140 for maneuvering in-vivo device 110 based on localization data that may be generated by in-vivo device 110 in response to localization electromagnetic fields/signals that are transmitted, or emitted, from LSS 130. In-vivo device 110 may be configured (e.g., it may include sensors) to sense a physical parameter in vivo. Temperature, pH, pressure, and impedance are example physical parameters. In-vivo device 110 may sense other physical parameters and/or be capable of performing various surgical operations in vivo. In-vivo device 110 may capture images (e.g., take pictures) in vivo (e.g., of the GI system). In-vivo device 110 may include a transmitter for transmitting data, for example to data recorder 120, which data may be related to sensed physical parameter and/or to captured images.

In-vivo device 110 may also include a location and steering unit ("LSU") 112. LSU 112 may include a sensing coils assembly ("SCA") for sensing electromagnetic localization signals that are generated by an external localization system and induced in electromagnetic sensing coils of the SCA. An electromagnetic field sensing coil is an exemplary type of electromagnetic field sensor/transducer; other types of electromagnetic field sensors may be used to sense an electromagnetic field. The electromagnetic field sensor mentioned herein is assumed to be a sensing coil only for convenience. The electromagnetic localization signals may be generated, for example, by electromagnetic localization signals source (LSS) 130. LSU 112 may also include a magnetic steering unit ("MSU") for maneuvering, or steering, in-vivo device 110 based on electromagnetic localization signals sensed by (induced in) the sensing coils of the SCA. In-vivo device 110 may also include a sensing signal processor ("SSP") 113 for processing signals that are induced in the electromagnetic sensing coils of the SCA, the processing may include, for example, sampling the sensed electromagnetic localization signals, evaluating signal characteristics of electromagnetic interference that may undesirably be picked up and superimposed on localization signals that are sensed by the SCA, and adding up sample values as part of a filtering process that cancels out the electromagnetic interference (e.g., remove the electromagnetic interference from the electromagnetic localization signals that the SCA outputs). As demonstrated in the drawings and described below, applying the filtering process on the signal that the SCA outputs enables both evaluating the genuine intensity of the electromagnetic localization signals and efficiently cancelling out the electromagnetic field inference.

Data recorder 120 may include, among other things (e.g., receiver, data frame parser, data storage unit, processor, etc.), a timing restoration unit ("TRU") 122, a synchronization signal unit ("SSU") 124, and a localization data unit ("LDU") 126. Data recorder 120 may include a transceiver (the transceiver is not shown in FIG. 1) for receiving data frames 116 from in-vivo device 110. Data recorder 120 may also include a transmitter for transmitting commands 118 to in-vivo device 110. Data recorder 120 may transmit a command to in-vivo device 110, for example, to change a mode of operation (e.g., an image capturing rate of an imager of the in-vivo device), or to update a parameter of the in-vivo device, etc. TRU 122 is used to restore the internal work cycles of in-vivo device 110 that drive in-vivo device 110, and, based on the restored work cycles, to synchronize between in-vivo device 110, LSS 130, and MMU 140.

Briefly, a data frame transmitted by in-vivo device 110 and received by data recorder 120 may include a fiducial indicia, or reference bit or a reference group of bits, that may facilitate generation, reconstruction or restoration, by TRU 122, of the clock pulses and a time reference originating from timing unit 114 and used by in-vivo device 110. TRU 122 may use the restored clock pulses and the reference time to determine time slots during which LSS 130 may be permitted to generate electromagnetic localization signals without being interfered with by MMU 140, and other time slots during which MMU 140 may be permitted to generate maneuvering signals without being interfered with by LSS 130.

LSS 130 may transmit electromagnetic localization signals in short bursts, where each electromagnetic localization signal burst may include n electromagnetic localization signals that may be spaced apart. In one embodiment LSS 130 may transmit an electromagnetic localization signal burst for each coordinate of a coordinate system. In another embodiment, each electromagnetic localization signal of an electromagnetic localization signal burst may be transmitted to sense a different coordinate. For example, LSS 130 may transmit, during a sensing window in a work cycle of in-vivo device 110, an electromagnetic localization signal burst that may pertain to the X-axis, then an electromagnetic localization signal burst that may pertain to the Y-axis, then an electromagnetic localization signal burst that may pertain to the Z-axis. LSS 130 may repeat the sequence of electromagnetic localization signal bursts for each work cycle, or for selected work cycles of the in-vivo device.

Figure 3A:
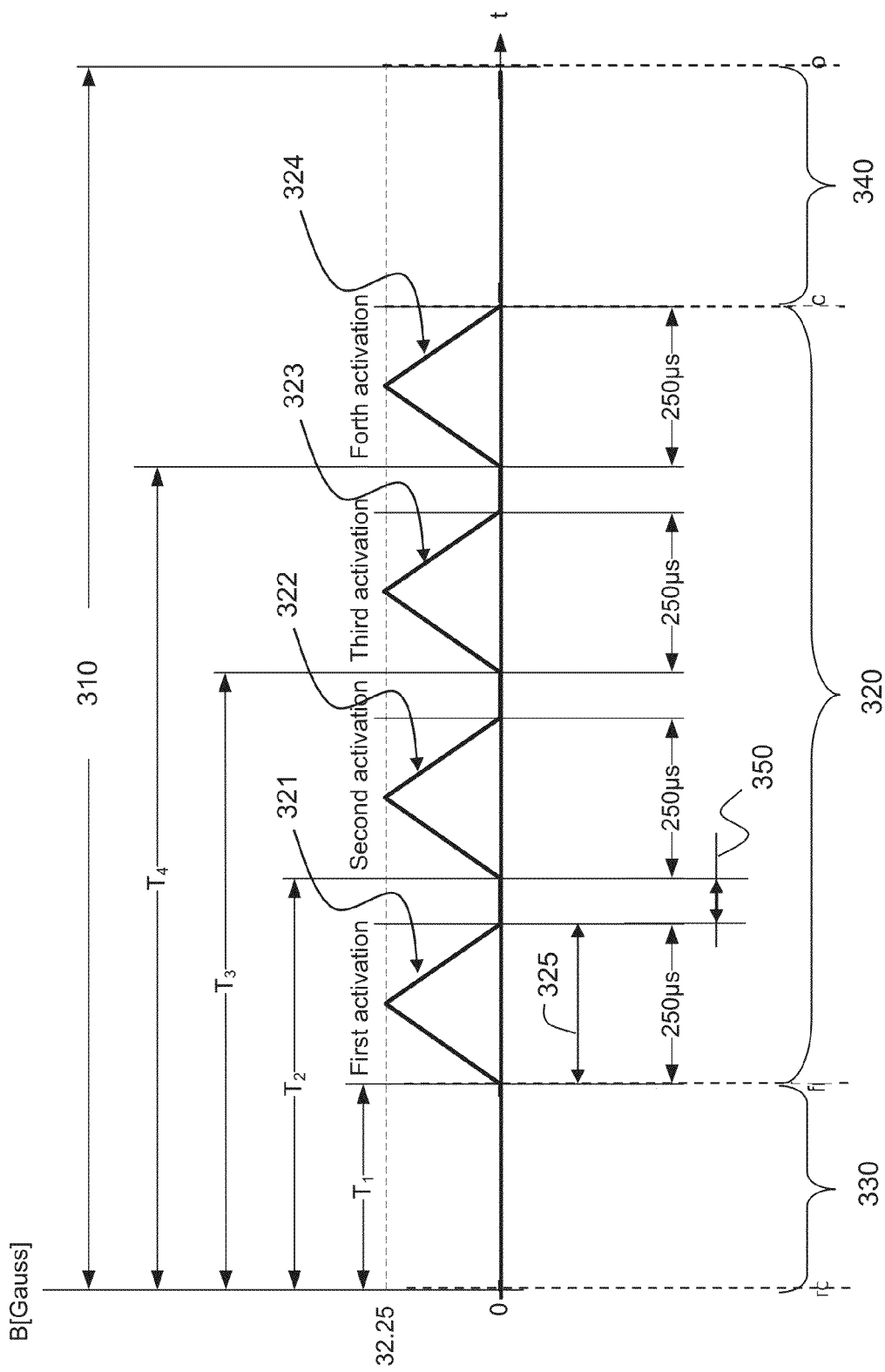

An electromagnetic localization signal burst may include a sequence of spaced apart triangularly shaped localization signals. An electromagnetic localization signal burst may also include a "pre-sensing" period, a type of 'quiet' period during, or for which, the intensity of an electromagnetic field interference may be estimated in order to estimate the interference superimposed on the localization signals at the output signal of the electromagnetic field sensors. An electromagnetic localization signal burst may additionally or alternatively include a "post-sensing" period (which is another type of quiet period that may function (used) in a similar way as the "pre-sensing" period) for enhancing the estimation of the interference superimposed on the localization signals. An electromagnetic localization signal burst may include one quiet period or two quiet periods, as explained above, or more than two quiet periods. Exemplary electromagnetic localization signal bursts are shown, for example, in FIGS. 3A, 3B, and 3C. Each electromagnetic localization signal burst may include, for example, four triangular localization signals, as shown in FIG. 3A, or other numbers of triangular localization signals (e.g., less than four triangular localization signals; e.g., three triangular localization signals, as demonstrated in FIGS. 3B and 3C, or more than four triangular localization signals).

Concurrently to the restoration of the in-vivo device's clock signal and reference time by TRU 122, synchronization signal unit (SSU) 124 may produce a synchronization signal 128 that complies with the time specifics of the sensing window(s), and transfer the synchronization signal to LSS 130, for example via a communication cable or wirelessly. Synchronization signal 128 enables LSS 130 to correctly time the generation or creation of one or more localization signals (in the form of electromagnetic field(s)). For example, LSS 130 may generate an electromagnetic field 132 at a time and for a duration set forth by, or complying with, synchronization signal 128, and therefore, in compliance with the restored sensing window(s), and therefore in compliance with the sensing window(s) originally used, or pre-allocated, by in-vivo device 110. Since the sensing window(s), which may be used by in-vivo device 110 during each work cycle or during selected work cycles, and the restored sensing window(s) used by data recorder 120 temporally overlap/match (within an operational margin), LSS 130 may generate/transmit localization signal 132 in time slot(s) during which in-vivo device 110 may read (e.g., by sampling) the electromotive force ("EMF") signals that the sensing coils assembly (SCA) of LSU 112, or another electromagnetic field sensor/transducer, may output in response to localization signal 132. In-vivo device 110 may allocate resources to process the read/sampled EMF signals wholly or partly.

As a result of the SCA, or another electromagnetic field sensor, sensing the electromagnetic signals during a work cycle of in-vivo device 110, in-vivo device 110 may embed data, which represents the EMF signals, in a data frame that may be transmitted (e.g., to a data recorder) during a transmission period, for example, of the following work cycle. Data that represents the raw EMF signals induced in the in-vivo device, and any variant, manipulation, or derivative of such signals or data (e.g., data representing the actual coordinates, or location/orientation, of the in-vivo device) may be referred to herein as "localization data" and "sensing data". "Localization data" may also for example refer to or include additional data that represents the orientation of the in-vivo device or enables to determine the orientation of the in-vivo device. Alternatively, localization data may be transmitted (e.g., to a data recorder) not by using the communication channel via which frames are transmitted, but by using a separate communication channel. Using a separate communication channel may enable more frequent transmission of larger amount of localization data.

Localization data unit (LDU) 126 may include or use a processor and other components and units that are required to interpret, calculate, deduce, infer, or otherwise determine the current position, and, optionally, also the current orientation, of in-vivo device 110 from, or by using, the localization data. After LDU 126 determines the location/orientation of in-vivo device 110, LDU 126 may transfer corresponding localization data 129 to another computing system. Localization data 129 may include data that represents the current location of in-vivo device 110, or the current orientation of in-vivo device 110, or both location and orientation of in-vivo device 110. The other computing system may, for example, display the location/orientation data (whether the raw data or a processed version thereof), and/or it may use past and current location/orientation data to display the route, or trajectory, traversed by the in-vivo device, and/or a point on a route representing the GI system, and/or it may use localization data 129 to maneuver, guide or steer in-vivo device 110.

Localization and maneuvering system 100 may optionally include fiducial electromagnetic field sensors 127, which are external to the in-vivo device, for sensing electromagnetic fields that may be generated either by LSS 130, or by MMU 140, or by both systems. Fiducial electromagnetic field sensors 127 may be connected to LDU 126 in order for LDU 126 to perform various calculations regarding, for example, fine tuning or optimization of the filtering process, or interference cancelling procedure, which is described in more detail below. For example, fiducial electromagnetic field sensors 127 may enable LDU 126 to monitor the electromagnetic field interference in order, for example, to measure or calculate its fundamental frequency, in order to determine whether, or how, sampling specifics, which determine the way (e.g.,) the output signal of each electromagnetic field sensor (e.g., each SCA's sensor coil) is to be sampled, have to be adjusted. (The term 'sampling specifics' may refer, inter alia, to for example the temporal location and width of a sampling window/period, to a sampling rate, and to the number and location of samples in the sampling window/period.) If sampling specifics have to be adjusted, LDU 126 may send a command to in-vivo device 110 to adjust the sampling specifics that are required to be adjusted. Alternatively, adjusting the sampling specifics may be determined internally, by the in-vivo device. Adjusting the sampling specifics to suit, or to cope with, changes in the fundamental frequency of the electromagnetic interference enables maintaining the filtering process, or interference cancelling process, optimized.

LDU 126 may transfer position/orientation data 129 to MMU 140 as a feedback in order for MMU 140 to generate a maneuvering magnetic field 142 to guide, steer, or maneuver, in-vivo device 110 to a new, target or desired location and/or to a new, target or desired orientation. That is, knowing the current location/position of in-vivo device 110 (e.g., from location/position data 129), MMU 140 may generate an electromagnetic maneuvering signal 142 to maneuver in-vivo device 110 to a required, or target, location or orientation. LSU 112 may include a MSU that may include, for example, permanent magnets and eddy current element(s). The permanent magnets and eddy current element(s) of the MSU may interact with electromagnetic signal 142 to produce magnetic forces and torques to steer the in-vivo device. MMU 140 may control the steering of in-vivo device 110 based, for example, on location/orientation signals that are provided by LDU 126 (e.g., position/orientation data 129).

The operation of MMU 140 may be synchronized to the operation of LSS 130 in order to ensure that MMU 140 and LSS 130 do not respectively generate maneuvering signal 142 and localization signal 132 at the same time. Operation of MMU 140 may be synchronized to the operation of LSS 130 also to ensure that MMU 140 generates a position (or orientation) correction signal 142 that is based on up to date localization/orientation data. SSU 124 may send a synchronization signal 144 to MMU 140 in order to synchronize between MMU 140 and LSS 130. Synchronization signal 144 may be identical to synchronization signal 128 or a manipulation or derivative thereof. Synchronization signal 144 may cause MMU 140 to generate, for each work cycle of the in-vivo device, a signal 142 in the form of a short maneuvering signal (a 'maneuvering burst'), or a series of maneuvering bursts, shortly after a sensing window is terminated.

Figure 2:
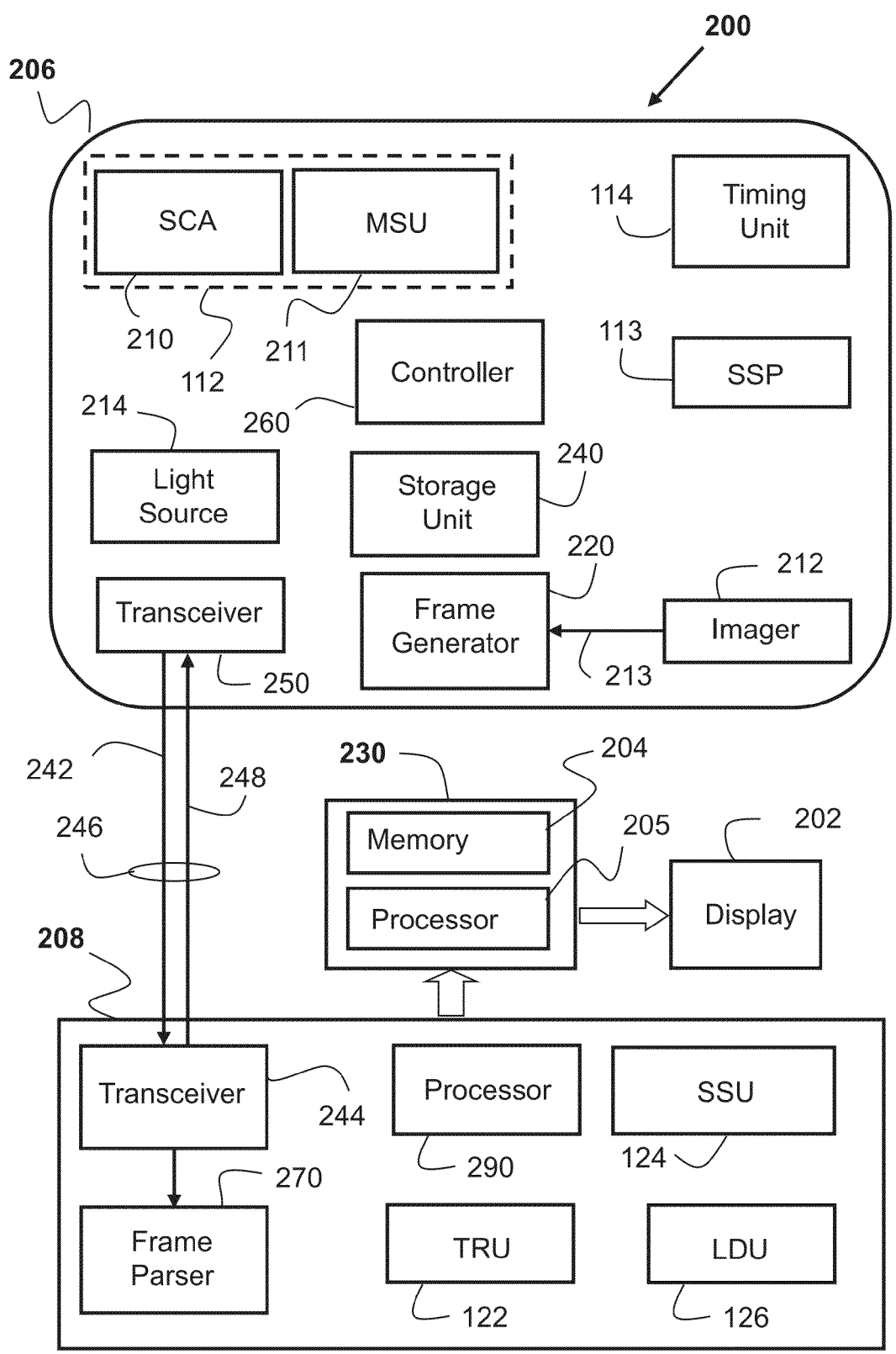
FIG. 2 is a block diagram of an in-vivo imaging system according to an embodiment of the invention.

FIG. 2 shows an in-vivo imaging system 200 according to an example embodiment. While FIG. 1 references an in-vivo device (in-vivo device 110) that transmits data frames that may be related to or include any type of sensory data (e.g., pH data), FIG. 2 shows in-vivo device 110 with an imager as an example sensor, in which case in-vivo device 110 may be referred to as an "in-vivo imaging device" or an "in-vivo imager", and (data) frames transmitted by or from in-vivo device 110 may be referred to as "image frames" (although image frames may include also other types of data, including localization data and/or other types of sensory data). The systems of FIGS. 1 and 2 may have similar components and thus the system shown in FIG. 1 may have some or all of the elements shown in FIG. 2 and vice versa. In-vivo imaging system 200 may include in-vivo device 206, data recorder 208, a user workstation 230, which may be, for example, a workstation or personal computer, and a display 202 for displaying, for example, images and/or a video clip or moving image stream which is produced from images, and for displaying the location and/or orientation of the in-vivo device, etc.

An in-vivo imaging device may have or include one or more imagers. By way of example, in-vivo device 206 includes one imager (e.g., imager 212) (numbers of imagers other than one or two may be used, with suitable modifications to the methods discussed herein). In-vivo device 206 may also include a light/illumination source 214 for illuminating a GI section/site/organ to be imaged, a frame generator 220 for producing an image frame for each captured image, a processor or controller 260, a storage unit 240 for storing data, a transmitter or transceiver 250 for transmitting images frames and, optionally, for receiving data and/or commands from data recorder 208, and an electrical power source for powering these components and circuits. A power source powering in-vivo device 110 may include a charge storing device (e.g., one or more batteries, which may be rechargeable or not) with an electrical circuit that jointly facilitates transfer of electrical power from an external power source to the in-vivo device through electromagnetic induction.

In-vivo device 206 may include a location and steering unit (LSU) 112. LSU 112 may include a sensing coil assembly (SCA) 210 for sensing electromagnetic localization signals generated, for example, by LSS 130 of FIG. 1. SCA 210 may include n electromagnetic sensing coils for sensing, through electromagnetic induction, electromagnetic localization fields/signals, where n is an integer equal to or greater than 1 (e.g., n=3 sensing coils) that may be, for example, mutually perpendicular. More than 3 sensing coils may be used, some of which may be used to enhance the device's location determining process and/or to facilitate determination of the orientation of the in-vivo device. Each electromagnetic sensing coil may be used to sense an electromagnetic field/signal in a different direction/orientation. For example, one coil may be used to sense an electromagnetic field/signal in the 'X' direction or in the Y-Z plane, another coil may be used to sense an electromagnetic field/signal in the 'Y' direction or in the X-Z plane, etc. Each electromagnetic localization signal generated by localization signals source (LSS) 130 may induce an EMF signal on one or more of the n electromagnetic sensing coils of SCA 210, and the current location, and optionally the current orientation, of in-vivo device 206 may be determined based on the EMF signal(s) sensed by (induced in) the electromagnetic sensing coils of SCA 210.

In-vivo device 206 may also include a magnetic steering unit (MSU) 211 to facilitate maneuvering of in-vivo device 206, for example through interaction with electromagnetic fields which may be generated by a maneuvering system similar to magnetic maneuvering unit (MMU) 140 of FIG. 1. MSU 211 may include, for example, permanent magnets and eddy current element(s) that may interact with electromagnetic signal 142 to produce magnetic forces and torques to steer in-vivo device 206 in a desired direction or to orient or position it in a desired orientation/direction.

In-vivo device 206 may also include timing unit 114 for scheduling time specifics (e.g., starting time and duration) of sensing windows during which EMF signals induced in sensing coils of SCA 210 may be measured, processed, and analyzed. Timing unit 114 may include a timing mechanism (e.g., clock generator) to generate a clock signal to time a work cycle of the in-vivo device. Within the work cycle may be defined a reference time. Transmitter 250 may transmit, within the work cycle, a data frame to a receiver (e.g., data recorder 208). The data frame may contain or include data facilitating restoration, by the receiver, of the clock signal and the reference time. Storage unit 240 may be used to store time specifics of, or time specifics defining, a sensing time window within the work cycle. Controller or processor 260 may be configured, within the work cycle, to measure time elapsing from the reference time by using (e.g., counting) clock pulses of the clock signal, and, based on the elapsed time (e.g., based on the counted pulses) and time specifics, to read the output of SCA 210 during a time period that partly or fully overlaps with the sensing time window allocated for that output read out. Controller 260 may also be configured to transmit, through transceiver 250, data representative of the sensed localization signal during the same work cycle or during a subsequent work cycle.

In-vivo device 206 may also include sensing signal processor (SSP) 113 for measuring the EMF signals, which are induced in the SCA, at sampling times within sensing windows that are allocated for that purpose, and for processing the sample values (e.g., filtering the samples to cancel out electromagnetic interferences, and determining the intensity of the induced EMF signal). SSP 113 may be used to reduce electromagnetically induced interferences. Even though it is preferable that MMU 140 be shut down completely while sensing of electromagnetic localization signals by SCA 210 takes place, for the reasons specified above (e.g., high currents and switching used to generate the maneuvering electromagnetic field) MMU 140 only decreases the intensity of the maneuvering electromagnetic field rather than shutting it down completely. Since the level to which the intensity of the maneuvering electromagnetic field is decreased still results in a significant interference that is induced in the sensing coils of SCA 210, this interference has to be filtered out in order for the resulting localization data/information to be accurate and reliable.

Data representing, or derived from, the EMF signals induced in SCA 210 may be transmitted 242, for example, to data recorder 208 by embedding the data in image frames and/or by using frames that may be dedicated to transfer of such data. Frames generator 220 may receive image data 213 that represents a captured image, and produce a corresponding image frame (or "frame" for short) that contains image data 213. A frame typically includes a header field that contains information and/or metadata related to the frame itself (e.g., information identifying the frame, the serial number of the frame, the frame's generation time, the bit-wise length of the frame, etc.), and a payload field. The payload field may include an uncompressed version of the image data and/or a compressed version thereof, and a decimated image. The payload may also include additional information related to or representative of, for example, values read out from SCA 210.

Controller 260 may controllably operate, among other things, illumination/light source 214 to illuminate areas traversed by in-vivo device 206, and schedule the images capturing times accordingly. Controller 260 may use timing unit 114 to time the operation of illumination source 214 to illuminate k times per second (e.g., k=4) to enable capturing k images per second, and the operation of transceiver 250 to concurrently transmit corresponding frames at the same rate or at a different rate. Controller 260 may temporarily store captured images and related image frames in data storage unit 240. Controller 260 may also perform various calculations and store interim calculation results in data storage unit 240. Controller 260 may also use timing unit 114 to read the EMF output of SCA 210 at the allocated sensing window(s)) from which the position and/or orientation of in-vivo device 206 may be calculated or deduced (e.g., by controller 260 or by an external system; e.g., data recorder 208). Controller 260 may also use timing unit 114 to time the writing (e.g., adding, appending, or otherwise embedding) of corresponding localization data (e.g., the sensing coils readout or a manipulated version thereof) into the corresponding frame; e.g., into a frame that is to be transmitted, for example, some time or immediately after, or concurrently to, the reading of the output of the sensing coils. After frames generator 220 produces a frame for a captured image and embeds localization data in the frame, controller 260 may use transceiver 250 to wirelessly transfer 242 the frame to data recorder 208. Controller 260, by executing software or instructions, may carry out steps which are performed by any one of SSP 113, timing unit 114 and frame generator 220, and other functions in in-vivo device 206, and thus may function as these units. Each of sensing signal processor (SSP) 113, timing unit 114 and frame generator 220, and other functions may be implemented as a dedicated hardware unit, or may be a code or instructions executed by a controller/processor, e.g., controller 260. The code/instructions may be distributed among two or more controllers/processors.

Controller 260 may use timing unit 114 between transmission periods (e.g., within idle periods separating transmission periods) to operate illumination source 214 to capture an image during a predetermined time window within an idle period during which transceiver 250 is dormant, disabled, or inactivated, the time window being referred to herein as an "imaging window". Controller 260 may also use timing unit 114 to read and process the output of SCA 210 during another predetermined time window within the idle period, the other time window being referred to herein as the "sensing window". Controller 260 may use timing unit 114 to time other activities of in-vivo imager 110 (e.g., receiving commands from data recorder 208, processing and executing the commands, etc.). Controller 260 may also use timing unit 114 to time the operation of SSP 113.

In one embodiment, cancelling out or reducing, or significantly reducing, the electromagnetic interference induced in the sensing coils of SCA 210 by the maneuvering electromagnetic field may involve sampling the output signal (sensing signal) of each electromagnetic field sensor (e.g., sensing coil) at a sampling frequency that is several times higher than the fundamental frequency of the interference, and processing the resulting samples as described below. Since in-vivo device 110 (or in-vivo device 206), LSS 130, and MMU 140 are designed as (they make up) a whole system, the signal characteristics (e.g., fundamental frequency) of the decreased maneuvering electromagnetic field generated by MMU 140 are generally known. Ideally (from the interference filtering standpoint), these characteristics should be invariable. However, in practice, they may vary within some tolerance/margin, which means that a particular sampling frequency (the rate at which the output of each sensing coil is sampled) that may enable optimal filtering of an interference having particular characteristics, may provide less than optimal filtering for interferences that have other characteristics (e.g., different fundamental frequency). That is, using a sampling frequency that is adapted or adjusted for the fundamental frequency of the interference may result in an optimal filtering of the interference because, under such circumstances, the most influential components of the interference may be cancelled out, or at least significantly reduced. However, if the two frequencies are not selected properly, the filtering process may be less than optimal and, with the interference being conspicuous, the resulting localization data may be inaccurate and, therefore, not reliable/usable. Therefore, in order to optimize the interference reduction/cancellation process for all interferences within a given margin, the sampling frequency, and the sampling scheme in general, used to sample the output signals of the SCA may have to be dynamically adjusted to cope with changes in the fundamental frequency of the interferences. In other words, the sampling scheme has to be adapted, or adjusted, (according) to the actual fundamental frequency of the interference.

Controller 260 may, for example by using timing unit 114, allocate and use a quiet period for measuring and analyzing the interference that is superimposed on the output signal output by the sensing coils of SCA 210 (or by another type of electromagnetic field sensors), while LSS 130 is completely shut down and MMU 140 transmits the maneuvering electromagnetic field. During the quiet period, controller 260 may analyze characteristics of the interference (e.g., frequency spectrum of the interference, etc.). Controller 260 may, then, use the interference analysis result to dynamically control (e.g., adjust) the time instants at which the output signals of the SCA are sampled, to optimize the interference filtering process despite changes in the characteristics of the interference signal. The term "dynamically control the time instants" means controlling the sampling frequency, the sampling window's length and/or location, the number of sampling points in the sampling window, and/or the phases of sampling points with respect to the (phase of the) fundamental frequency of the interference signal. Any combination of transceiver 250, controller 260, timing unit 114, frame generator 220, SSP 113, storage unit 240, imager 212 and a controlling part of light source 214 may be embedded in one or more microchips.

Data recorder 208 may also include a receiver or transceiver 244, a frame parser 270, and a processor or controller 290 for managing them. Data recorder 208 may include additional components (e.g., USB interface, Secure Digital ("SD") card driver/interface, controllers, etc.), elements or units for communicating with (e.g., transferring data frames, data, etc. to) a processing and/or displaying systems that may be configured to process images and localization data originating from in-vivo imager 110, and related data.

Transceiver 244 may receive 242 a data frame corresponding to a particular captured image, and frame parser 270 may parse the data frame to extract the various data contained therein (e.g., image data, decimated image associated with the particular captured image, localization data, etc.). In some embodiments, some data frames, which may be referred to herein as "localization frames", may be dedicated to contain and transfer only or mostly localization data. Localization frames may, for example, include localization data but not image data. Processor or controller 290, by executing software or instructions, may carry out steps which are performed by any one of TRU 122, SSU 124, and LDU 126, and other functions in data recorder 208, and thus may function as these units. One or more of processors or controllers 205, 290, and 260 may perform methods as discussed herein.

User workstation 230 may include a display or be functionally connected to one or more external displays, for example to display 202. Workstation 230 may receive frames (e.g., image frames, localization frames, etc.) or images from data recorder 208 and present them in real-time, for example as live video, or produce a video stream that also contains location and orientation information that may also be displayed on, for example, display 202. Workstation 230 may include a memory (e.g., memory 204) for storing the frames transferred from data recorder 208 and possibly related metadata, and a processor (e.g., processor or controller 205) for processing the stored frames and related data. Workstation 230 may display selected images or a video clip (e.g., a moving image stream) compiled from such images, e.g., to a human operator, health care or caregiving person, physician, etc.

FIG. 3A schematically illustrates an electromagnetic localization signal burst 310 according to an exemplary embodiment. If the electromagnetic localization fields/signals that LSS 130 transmits/radiates are sinusoidal, then the EMF signals induced in each sensing coil of SCA 210 is also sinusoidal because an electrical coil outputs an EMF voltage that is a derivative of the electrical current induced in it. The electromagnetic interference, may be caused by the maneuvering electromagnetic field that MMU 140 generates during a blank period (which is the shutdown period of MMU 140), may include aperiodic signals and periodic signals whose fundamental frequency is the switching frequency of the switching circuit that MMU 140 uses to generate the maneuvering electromagnetic field. Therefore, the interference may severely distort or deform the shape of the sinusoidal localization signals that are induced in the sensing coils of the SCA. Filtering a sinusoidal interference out from sinusoidal localization signals may relatively take a long time, and it may require additional data processing capabilities, battery power and other resources that may not be available to the in-vivo device. In addition, sampling a sinusoidal localization signal is susceptible to sampling jitter (jittered samples add additional errors).

The problem described above may be mitigated by using, for example, triangularly shaped localization electromagnetic fields, because, by using triangular electromagnetic fields, the sensing coils of the SCA output an alternating signal that is square or substantially square, which is advantageous over using sinusoidal signals, for example, because the sampling jitter in a square, or square like, waveform does not add error. (In terms of peak-to-peak amplitude, the timing constraints involved in where the positive pulse and the negative pulse of a square signal are sampled are significantly lessened because all samples of the positive pulse have substantially the same value, and the same applies to the negative pulse, as explained below, for example, in connection with FIGS. 4A, 4B and 4C.) The shape of the localization electromagnetic field does not necessarily have to be rectangular. Rather its shape preferably is such that the electromagnetic field sensor used by the in-vivo device can convert it into, or use it to output, an alternating square, or square like, signal. In other words, while the electromagnetic field sensor should output an alternating square signal, the shape of the input signal of the electromagnetic field sensor may depend on the type of the sensor.

The localization electromagnetic field may be radiated, or transmitted, as an electromagnetic localization signal burst. An electromagnetic localization signal burst may include any combination of one or more localization signals that may be spaced apart by temporal pauses, one or more quiet periods that may be interspersed between the localization signals, a pre-sensing period that precedes all the localization signals of the localization signal burst, and a post-sensing period that succeeds all the localization signals of the localization signal burst. Exemplary electromagnetic localization signal bursts are shown in FIGS. 3A through 3C, which are described below.

Referring to FIG. 3A, electromagnetic localization signal burst 310 may be generated or transmitted, for example, by LSS 130. Localization signal burst 310 may include a series of distinct triangular electromagnetic fields/signals that are, respectively, generated/transmitted during distinct activation periods. Each triangular electromagnetic field/signal may be generated or transmitted during a particular activation period. In general, an electromagnetic localization signal burst may include an activation window, which is also referred to herein as a "sensing window", during which the LSS (LSS 130) generates/transmits the series of triangular electromagnetic fields/signals, and a quiet window/period during which the LSS may not generate/transmit localization electromagnetic fields/signals. MMU 140, which is synchronized with the in-vivo device and LSS 130, may decrease the intensity of the maneuvering magnetic field (and apply a restraining force to 'freeze', or retain, the in-vivo device in place) during blank periods in preparation for the generation of the localization magnetic field by the LSS and sensing of the resulting localization signals by the SCA (or, in general, by the electromagnetic field sensors). MMU 140 may decrease the intensity of the maneuvering magnetic field during blank periods in order to reduce the electromagnetic interference superimposed on the localization signals induced in the SCA. As explained herein, the maneuvering magnetic field, though decreased, also has a ripple that may have to be filtered out in order to enable obtaining accurate and reliable localization data.

By way of example, electromagnetic localization signal burst 310 may include an activation window 320 that includes four, temporally distinct, triangular localization electromagnetic fields/signals (or 'triangular localization signals', for short), which are designated as a triangular localization signal 321, a triangular localization signal 322, a triangular localization signal 323, and a triangular localization signal 324. Each triangular localization signal may have a duration $T_L$. For example, the duration of localization signal is shown at 325. During activation of a localization signal, each sensing coil of the SCA senses, through magnetic induction, the triangular localization signal, and outputs a corresponding square EMF signal. Therefore, activation window 320 is also regarded as a localization signal sensing window (localization signal sensing window 320 may be part of (it may overlap, at least partly,) the sensing window mentioned above in connection with the work cycles of the in-vivo device).

The triangular localization signals may be spaced apart to facilitate better electrical distinction. For example, the time spacing, or gap, between triangular localization signals 321 and 322 is shown at 350. The time spacing or gap between adjacent localization signals (e.g., between localization signals 321 and 322, between localization signals 322 and so on) is also referred to herein as the "localization signal pause" ("LSP"). The LSP between two adjacent triangular localization signals may be used to perform interim calculations or processing that may be associated, for example, with interferences and/or localization signals that are sensed by the sensing coils assembly (SCA), and/or with reshaping of analog signals and/or converting analog signals to digital format, etc. By way of example, each of the four triangular localization signals 321 through 324 is symmetric and 250 microseconds wide, though triangular localization signals may be asymmetric and have widths other than 250 microseconds. Alternatively, the width of the triangular localization signals may vary between triangular localization signals within the same localization signal burst, or they may change from one localization signal burst to another.

Localization signal burst 310 may also include a 'quiet' window that, in the example of FIG. 3A, is divided into two, separate, quiet periods that are designated as a pre-sensing period 330, and a post-sensing period 340. The term 'pre-sensing period' means the period prior to the generation of the localization signals of the pertinent localization signal burst and, therefore, prior to sensing of the localization signals by the electromagnetic field sensors. The term 'post-sensing period' means the period, in the pertinent localization signal burst, that succeeds the localization signals.

During the pre-sensing period and post-sensing period, the interference caused by the maneuvering electromagnetic field may be managed (e.g., sensed by the electromagnetic field sensor/transducer, measured, processed, and used) as explained below. (It is noted that it is not necessary to manage interferences during quiet periods, though doing so may provide a filtering process that is more robust.) Measuring and processing the interference caused by the maneuvering electromagnetic field may be beneficial for the reasons described below.

Determining or quantifying an interference during quiet period 330 and during quiet period 340 may enable extrapolating the interference between these instances, for example, during the activation periods during which the triangular localization signals 321, 322, 323, and 324 are transmitted. For example, extrapolating the interference for a signal induced in a sensing coil of the SCA during the activation period associated with triangular localization signal 321 may enable optimizing the filtering of the signal during that activation period. Filtering most of the more energetic/influential components of the interference may be relatively simple because it does not require extrapolation of interferences. (The way the extrapolation-free filtering is performed is demonstrated in FIG. 4C, which is described below.).

An electromagnetic localization signal burst similar or identical to electromagnetic localization signal burst 310 may be repeated e.g., once per data frame of in-vivo device 110. That is, an electromagnetic localization signal burst may be generated for each data frame. (Commencing and terminating an electromagnetic localization signal burst may be synchronized with a sensing window allocated for the pertinent data frame). Electromagnetic localization signal bursts may have a pattern that differs from the pattern of electromagnetic localization signal burst 310. Electromagnetic localization signal bursts having other example patterns are shown, for example, in FIG. 3B and in FIG. 3C.

FIG. 3B shows an electromagnetic localization signal burst 360 according to another example embodiment. An activation window may, in general, include n triangular localization signals (where n may be equal to or greater than 1). In FIG. 3B, electromagnetic localization signal burst 360 includes three triangular localization signals (n=3), which are designated as 361, 362, and 363, and a pre-sensing quiet period 370 that precedes triangular localization signals 361 through 363. Triangular localization signals 361, 362 and 363 may be temporally equidistantly spaced apart: triangular localization signals 361 and 362 may be separated by localization signal pause (LSP) 364, and triangular localization signals 362 and 363 may be separated by LSP 365. A localization signal pause may also be used as a quiet period, as demonstrated in FIG. 3C, which is described below. During localization of an in-vivo device (e.g., in-vivo device 110), a series of localization signal bursts that are identical or similar to localization signal burst 360 may be transmitted, each of which may be associated with (transmitted in synchronization with) a sensing window that is scheduled, or timed, for a particular data frame of the in-vivo device. A localization signal burst may be transmitted for each data frame, or for a group of data frames (e.g., each $n^{th}$ data frame; e.g., each $5^{th}$ data frame).

FIG. 3C shows an electromagnetic localization signal burst 380 according to yet another example embodiment. In this embodiment, electromagnetic localization signal burst 380 includes three triangular localization signals, which are designated as 381, 382, and 383, and three quiet periods, which are designated as 391, 392, and 393. In this example, a quiet period may be associated with each triangular localization signal. For example, quiet period 391 may be associated with (it may precede) triangular localization signal 381; quiet period 392 may be associated with (it may precede) triangular localization signal 382; and quiet period 393 may be associated with (it may precede) triangular localization signal 383. Any number of triangular localization signals and/or quiet periods may be used, and a quiet period may be associated with one or more triangular localization signals that may precede it, and with one or more triangular localization signals that may succeed it. By "a quiet period is associated with a triangular localization signal" is meant that an electromagnetic interference may be sensed during the quiet period and processed in order to facilitate determination or evaluation of the electromagnetic interference existing when the (associated) triangular localization signal is generated or transmitted. The characteristics of an interference that is evaluated during or for a particular quiet period may be used to filter interferences that may be sensed by a sensing coil of the SCA during one or more (e.g., two, three, etc.) activation periods that precede the particular quiet period, or during one or more (e.g., two, three, etc.) activation periods that follow the particular quiet period.

In general, a quiet period (e.g., a pre-sensing period, a post-sensing period, or both the pre-sensing period and post-sensing period) may be common to (they may be used to evaluate an interference for) any number of triangular localization signals. In FIG. 3A, pre-sensing period 330 and pre-sensing period 340 are common to four triangular localization signals 321 through 324; in FIG. 3B pre-sensing period 370 is common to three triangular localization signals 361 through 363; and in FIG. 3C a different pre-sensing period is allocated to each of triangular localization signals 381 through 383. A quiet period may function both as a pre-sensing period for a succeeding triangular localization signal, and as a post-sensing period for a preceding activation period. For example, quiet period 392 may function both as a pre-sensing period for triangular localization signal 382 and as a post-sensing period for triangular localization signal 381.

FIG. 4A schematically illustrates an exemplary triangular localization signal that is applied to an SCA, and an output signal of the SCA according to an example embodiment. During activation period 400, LSS 130 may generate a triangular magnetic field, or a triangular localization signal 410 (triangular magnetic field 410 is shown in FIG. 4A as a broken line). A sensing coil of the SCA of the in-vivo device may sense triangular localization signal 410 and, in response to it, output a square signal 420 that is a derivative of triangular magnetic field 410: when triangular magnetic field 410 rises linearly, as shown at 412, the derivative is a constant positive value (e.g., +2.0 volts in the example of FIG. 4A), and when triangular magnetic field 410 decreases linearly, as shown at 414, the derivative is a constant negative value (e.g., −2.0 volts in the example of FIG. 4A). Therefore, signal 420 may be thought of as an ideal square wave voltage that spans between the exemplary positive level +2.0 volt and the exemplary negative level −2.0 volt. The positive and negative levels between which signal 420 spans, or alternates, depend on various factors such as the distance between the SCA and the LSS, the orientation of the SCA relative to the magnetic field generating coils of the LSS 130, the specifics of the derivation electronic circuit, power source, etc.

The time width of square signal 420 matches the time width of the frequency triangular localization signal 410 because the first signal is a derivative of the latter signal. The in-vivo device may transmit data, for example to data recorder 120, that represents the localization signal (e.g., signal 420) induced in the sensing coil. That data may represent, for example, the peak-to-peak amplitude of signal 420 (referring to signal 420, the peak-to-peak amplitude is +2−(−2)=4.0 volts, as shown at 422). However, using peak-to-peak amplitude 422 of signal 420 as a measure of its magnitude is susceptible to noises and electromagnetic interferences and, therefore, this methodology is not optimal.

Therefore, instead of referring to the peak-to-peak amplitude of signal 420 conventionally, a first sampling window, or a positive sampling window, Sw_1 (shown at 424), is used to sample signal 420 at a plurality of points in a positive portion/pulse 428 of signal 420, and a second, non-overlapping, sampling window, or a negative sampling window, Sw_2 (shown at 426), which has the same duration as positive sampling window 424, is used to sample signal 420 at a plurality of points in a negative portion/pulse 429 of signal 420. As demonstration in FIG. 4A, each pulse of signal 420 is sampled at nine points.

In one embodiment, signal 420 (and similar signals that are square or generally square-shaped), may be represented by a number ($N_R$) that may be calculated using, for example, equation (1):

$$N_R = \sum_{i=1}^{k} a_i - \sum_{i=1}^{k} b_i (= N_P - N_N) \quad (1)$$

where $N_R$ is the number representing signal 420, $a_i$ and $b_i$ are, respectively, positive and negative sample values that are respectively sampled from the positive pulse and negative pulse of signal 420 within a respective sampling window (Sw), i is an index that varies from 1 to k, where k is the number of sampling points in each sampling window.

The value of k may change, including between sampling windows, as explained below. The same number of samples may be used to sample the positive and negative pulses, or levels, of subsequent cycles of the alternating square signal.

Applying equation (1) to signal 420 (which has an ideal square waveform and, therefore, all nine positive samples have the same value that, in this example, is +2.0, and all nine negative samples have the same value that, in this example, is −2.0), the representative number, $N_R$, is, therefore:

$N_R = (+2) \times 9 - (-2) \times 9 = 18 - (-18) = 36$

The resulting value 36 calculated above represents signal 420, which is free of interferences. However, as described below, for example in connection with FIG. 4C, if a periodic interference is superimposed on signal 420, applying equation (1) on the resulting noisy signal results in the same calculation result (36). This means that the application of equation (1) both calculates the number $N_R$ that uniquely represents the genuine signal 420, and cancels the interference. Application of equation (1) on signals that the electromagnetic field sensors (e.g., the sensing coils of the SCA) output cancels out every periodic signal in the spectra of the electromagnetic interference whose amplitude is constant or changes (e.g., decays) linearly over time. Some types of periodic signals in the spectra of the electromagnetic interference may be cancelled out by extrapolating the electromagnetic interference during the pertinent localization signal generation period from an electromagnetic interference that is characterized (by sampling, processing, and measuring it, etc.) during one or more quiet periods as demonstrated, for example, in FIG. 5B, which is described below.

Figure 4C:
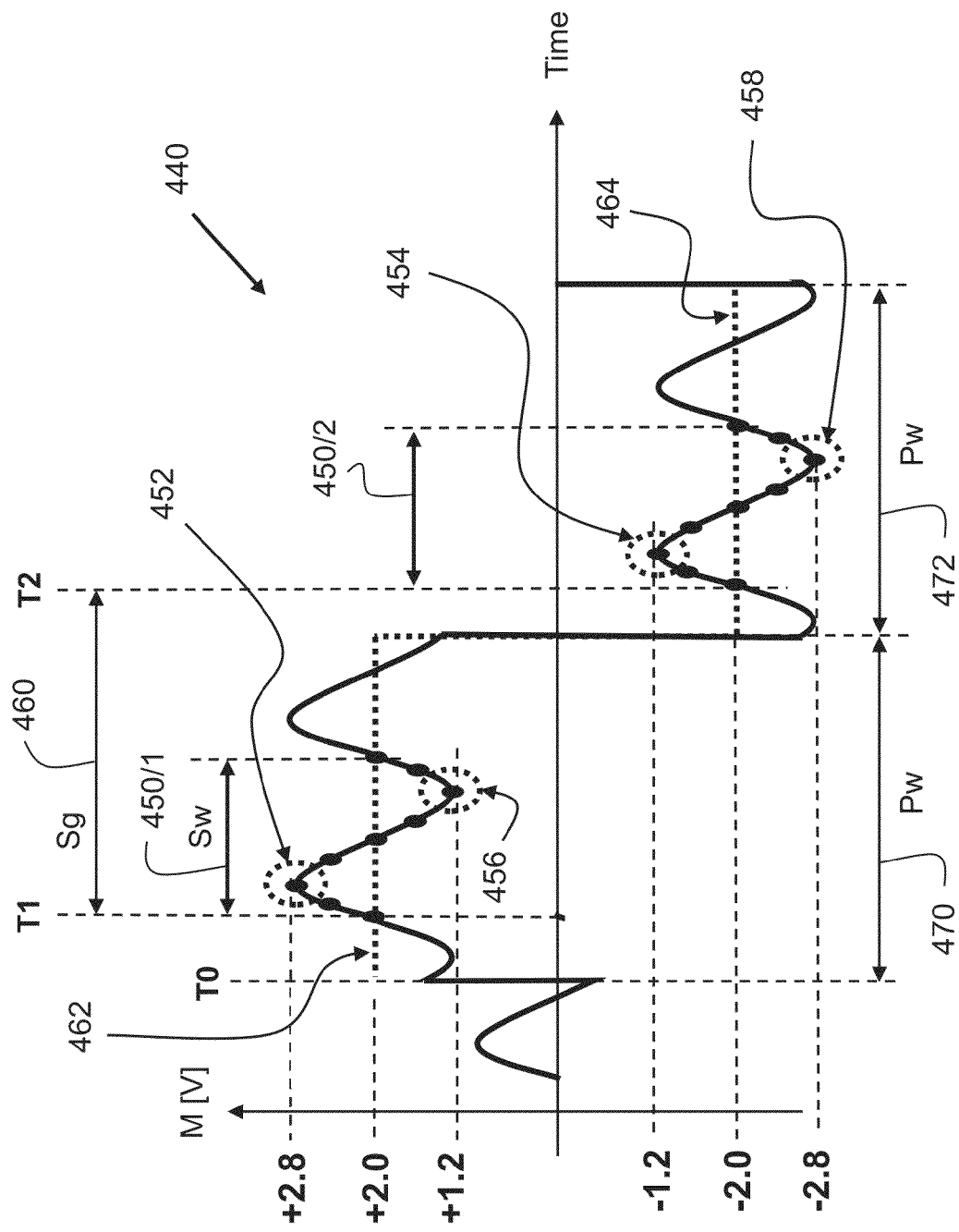
FIG. 4C schematically illustrates a sampling method for filtering a noisy localization signal according to an embodiment of the invention.

FIG. 4B shows an exemplary interference signal 430 that may be superimposed on the localization signal at the output of the sensing coils of the SCA according to an example embodiment. Interference signal 430 may be a signal having the fundamental frequency, $f_I$, of the electromagnetic field interference, and, as such, it may have a fundamental cycle, $T_I$, which is shown at 432. As described herein, for example in connection with FIG. 4C, the relationship between the fundamental frequency of the interference to positive sampling window 424 and negative sampling window 426 has to meet certain (sampling) conditions in order to optimize the interference filtering process. As explained above, during blanking periods MMU 140 decreases its maneuvering electromagnetic field/signal in order to decrease the interference induced by it in the SCA during the time when LSS 130 generates the triangular localization signals. However, despite the decreased maneuvering electromagnetic field/signal, an interference signal such as interference signal 430, or a periodic interference signal that may resemble interference signal 430, or any other periodic interference, may still be present in the decreased maneuvering electromagnetic signal and, consequently, induced in the SCA as interference. The reason for the presence of the periodic interference in the maneuvering electromagnetic field/signal is that, when MMU 140 generates the maneuvering electromagnetic field/signal to maneuver in-vivo device 110, it controls the intensity of the maneuvering electromagnetic field/signal by using the a corresponding switching/control technique. Using this switching/control scheme results in a switching signal that contains a fundamental frequency and high harmonics that are respectively smoothed and filtered out prior to the transmission of the decreased maneuvering electromagnetic signal. In-vivo device 110 uses an internal filter to filter the switching signal further. Therefore, the electromagnetic interference, which is imposed on the square signal at the output stage of the SCA, is sinusoidal. Cancelling out a sinusoidal interference from the square signal by using the filtering methods disclosed herein is relatively simple and efficient.

During blanking periods MMU 140 switches, or transitions, from a fully operational mode, in which MMU 140 uses a switching circuit to controllably change the maneuvering electromagnetic field/signal in order to maneuver the in-vivo device, to a standby, or dormant mode in which it uses the switching circuit to decrease the intensity of the maneuvering electromagnetic field/signal to a non-zero value that, as explained above, includes an interference that oscillates at the fundamental frequency of the switching circuit.

The frequency of the localization electromagnetic field/signal generated by LSS 130 (e.g., signal 410), and therefore the frequency of the signal that is derived from it (by the sensing coils of the SCA) may be, for example, 4 KHz. The switching frequency, and therefore the frequency of the interference signal generated by MMU 140 (e.g., signal 430) is typically higher (e.g., in the order of tens of kilohertz) than the frequency of the localization electromagnetic fields/signals generated by LSS 130. For example, the frequency of the interference may be, or vary around, 20.8 KHz.

The frequency of the localization electromagnetic field/signal may undesirably vary or jitter within some margin due to tolerance of the used localization signal source (e.g., LSS 130), jitter, and while the LSS warms up. For similar reasons, the primary/fundamental frequency of the interference signal may also undesirably vary or jitter within some margin. Since the interference filtering process described herein is based on specific relationships between the two types of frequencies, the filtering system, which implements the filtering process by sampling the signals that the SCA outputs, is configured to adjust the sampling times, as per sampling criteria, in order for the filtering process to be optimal despite changes in any frequency (the frequency of the localization signals, or the fundamental frequency of the interference), or in both frequencies. The filtering process and the filtering system are described below.

FIG. 4C schematically illustrates a signal 440 that is a superposition of an interference free square signal similar to square signal 420 of FIG. 4A, and an electromagnetic interference similar to electromagnetic interference 430 of FIG. 4B. If no electromagnetic field induced interference is superimposed on the square signal (square signal 420 in FIG. 4A is an interference free signal), the sampling window 450 may have substantially any duration (within pulses 470 and 472), and it may start substantially at any point in the positive pulse (pulse 470) of the signal, and at any point in the negative pulse (pulse 472) of the signal. However, if an interference is superimposed on the square signal, the signal characteristics (e.g., the fundamental frequency) of the interference have to be taken into account when setting the time specifics of the sampling windows, in order to optimize the interference filtering or cancelling process. That is, in order to optimize the filtering process that filters out, or cancels out, the interfering signal, certain sampling conditions may have to be met, which may depend on the type of electromagnetic interference, as described below. For example, sampling window (Sw, shown at 450) has to be wide enough to enable sampling at least one, whole, cycle, $T_I$, of the fundamental frequency, $f_I$, of the interference signal; that is, the condition Sw≥$T_I$, where $T_I=1/f_I$ may have to be met. Sw may be smaller than $T_I$ if, for example, the interference is constant, because, in such a case, one sample in each sampling window (in this case Sw=0) may suffice to cancel out the interference. Preferably Sw=m$T_I$, where m is an integer equal to or greater than, say, 1. Selecting Sw such that Sw contains a whole number of $T_I$ may be beneficial because such a selection may facilitate cancellation of high-order interferences, as described below.

The sample values, or samples, of a first portion (e.g., the positive portion) of the resulting signal (the signal that each sensing coil of the SCA outputs, which may include both the square signal and the periodic, and possibly aperiodic, interferences) and the sample values, or samples, of a second portion (e.g., the negative portion) of the resulting signal have to be in phase; that is, a sampling interval, or sampling gap (Sg) 460, which is the time elapsing from the first sampling point in the first/positive portion 470 of signal 440 (e.g., at starting point T1 of positive sampling window 450/1), to the first sampling point in the second/negative portion 472 of signal 440 (e.g., at starting point, T2, of the negative sampling window 450/2), has to include a whole number, n, of cycles of the fundamental frequency of the interference signal. That is, the condition Sg=n$T_I$, where n is an integer equal to or greater than, say, 1, has to be met. In FIG. 4C, Sw is equal to $T_I$ (Sw=$T_I$, the first condition, where n=1), and n is approximately 2 (Sg≅2$T_I$, the second condition). Meeting the first condition (Sw≥$T_I$) is beneficial because sampling less than one cycle of the interference may result in insufficient number of sampling points, and meeting the second condition (Sg=n$T_I$) implies that samples sampled from the first/positive portion of signal 440 and samples sampled from the second/negative portion of signal 440 are in phase, and in-phased samples enable cancelling out various types of interferences, as described and explained below. Sampling the first/positive and second/negative portions of a noisy signal (e.g., alternating signal 440) such that the samples are in phase with each other is beneficial because it may result in the absolute difference between the samples sampled from the first portion of the noisy signal and the samples sampled from the second portion of the noisy signal (e.g., signal 440) remaining the same for each sample in the first portion of the signal and its conjugated/paired (in-phased) sample in the second portion of the signal. As a result of this, a value $N_R$ representing, by being calculated from, the differences between the positive samples and the negative samples, and also the true peak-to-peak amplitude, or intensity, of the interference-free signal, remains constant across the samples despite the oscillating nature of the samples (due to them being sampled from a 'flat' signal that is biased by a sinusoidal signal). Therefore, using the sampling criteria Sw=mTi and Sg=nTi nullifies the effect of sinusoidal interferences, and, in general, the effect of any periodic interference whose frequency abides to the sampling criteria. Using the sampling criteria Sw=m$T_I$ and Sg=n$T_I$ also helps nullifying the effect of some aperiodic interferences, as described and explained below.

For example, in-phase sampling of positive values between +1.2v and +2.8v and negative values between −1.2v and −2.8v results in the absolute difference between the positive samples and the negative samples of signal 440 remaining the same (+4.0v) for each positive sample and its conjugated/paired/'in-phased' negative sample: the absolute difference between positive sample +2.0v and the negative sample −2.0v is 4.0v; the absolute difference between positive sample +2.4v and the negative sample −1.6v is also 4.0v; the absolute difference between positive sample +2.8v and the negative sample −1.2v is also 4.0v, and so on. Therefore, in FIG. 4C, the variable $N_R$, which genuinely represents the true peak-to-peak amplitude (4.0v) of the interference-free signal, remains constant across the sampling values despite the oscillating nature of the samples. The full sampling process is exemplified below.

Applying equation (1) to the sampling points, or samples, of FIG. 4C, the value representing signal 440 (which, for the sake of the example, is assumed to be a superposition of localization signal 420 of FIG. 4A and interference signal 430 of FIG. 4B) is:

$$N_R=2.0\times3+2.4\times2+2.8\times1+1.6\times2+1.2\times1+(2.0\times3+2.4\times2+2.8\times1+1.6\times2+1.2\times1)=(6+4.8+2.8+3.2+1.2)\times2=18\times2=36$$

As demonstrated above, signal 420, which is not subjected to interferences, and signal 440, which is, have the same representative value (in both cases the representative value of the signals is 36). This shows that, by using the two sampling criteria above, a periodic interference superimposed on the square signal can easily and efficiently be cancelled out regardless of the magnitude and frequency of the interference (provided that its frequency is higher than the frequency of the localization signal).

Such filtration may nullify, or cancel out, the periodic interference because, by using the sampling criteria and applying equation (1) on the positive samples and negative samples of the signal, each positive deviation in the positive portion 470 of signal 440 is compensated for by a paired, conjugated, or in-phased positive deviation in the negative portion 472 of signal 440. For example, positive sample 452, which is a positive deviation from positive level 462 of the square signal) is compensated for by a paired, conjugated, or in-phased positive sample 454, which is a positive deviation from negative level 464 of the square signal. Likewise, each negative deviation in the positive portion 470 of signal 440 is compensated for by a paired, or conjugated, or in-phased negative deviation in the negative portion 472 of signal 440. For example, positive sample 456, which is a negative deviation from positive level 462 of the square signal) is compensated for by a paired, conjugated, or in-phased negative sample 458, which is a negative deviation from negative level 464 of the square signal.

The term 'deviation', as used herein, means amplitude-wise deviation from the 'expected', or genuine, positive, or negative, level of the interference free square signal, which is caused by the interference. 'Positive deviation' is a deviation that increases, or elevates, the output signal of the pertinent sensing coil (e.g., makes it more positive or less negative) due to the interference. 'Negative deviation' is a deviation that makes the output signal of the pertinent sensing coil less positive or more negative due to the interference.

For example, positive deviation 452 is fully compensated by positive signal deviation 454 because deviation 452 makes the positive level of square signal 440 more positive by 0.8v (its level is increased from +2.0v to +2.8v in the example shown in FIG. 4C), and deviation 454 makes the negative level of square signal 440 less negative by 0.8v (its level is elevated from −2.0v to −1.2v in the example shown in FIG. 4C). Sample 452 and sample 454, therefore, make up a sampling pair that has no effect on the genuine value of the representative number A in equation (1). (As explained above, positive samples and negative samples are in phase with which other in the sense that each positive sample has a negative sample that is in phase with it.)

The electromagnetic field interference, $I_n$, induced by the maneuvering electromagnetic field in the electromagnetic field sensors/transducers of the in-vivo device may have aperiodic interferences and periodic interferences of $n^{th}$ order with respect to time, t, as shown in expression (2) below, where a zero-order interference is an interference expressed by expression (2) with n=0, a first order interference is an interference expressed by expression (2) with l=0, and so on:

$$I^n = C_n t^n + K_n t^n \cdot \cos(2\pi f \cdot t + \phi_n) \quad (2)$$

where $C_n t^n$ is an aperiodic interference of the $n^{th}$ order and $K_n t^n \cdot \cos(2\pi f \cdot t + \phi_n)$ is a periodic interference of the $n^{th}$ order.

As shown in expression (2), each $n^{th}$-order interference includes an $n^{th}$-order aperiodic interference and an $n^{th}$-order periodic interference. The zero-order interference and the first-order periodic interference may be fully cancelled out from the noisy localization signal that each sensor coil outputs by applying equation (1) only on the positive portion and negative portion of the noisy localization signal.

Using equation (1) as described above may not suffice for interferences of orders that are higher than 1, and a complimentary filtering process may be required to filter out such interferences. Briefly, the complimentary filtering process used to filter each sensor's output signal may include sampling the output signal during one or more time periods, which are referred to herein as 'quiet periods', during which the localization signal source (e.g., LSS 130) does not transmit localization signals; applying equation (1) on the samples to calculate a number for each quiet period (which is referred to herein as 'fiducial number') that represents the interference during the quiet period. Then, the interference caused by the high-order (e.g., second-order, third-order, etc.) interference during the sensing period (e.g., sensing period 320 in FIG. 3A) may be extrapolated, deduced or inferred, from the fiducial number(s) representing the interference(s) sampled during the quiet period(s). Then, the extrapolated, deduced or inferred interference may be deducted from the number that represents the noisy localization signal during the sensing window.

Extrapolation of an interference during the sensing window (the interference expected to be superimposed on the alternating square signal) is based on the phenomenon that uncompensated for samples, which are sampling errors due to high-order interferences, change over time in a mathematical consistency. For example, the amplitude of a 2-order interference is a function of $t^2$, and the numbers representing the interferences over time change as a function of the derivative of $t^2$; that is, as a function of 2·t. Therefore, calculating one fiducial number during one quiet period may be used to extrapolate an interference-representing number for any interference that is expected during any particular period because the sampling errors change linearly over time. Likewise, the amplitude of a 3-order interference is a function of $t^3$, and, therefore, the numbers representing the interferences over time change as a function of the derivative of $t^3$; that is, as a function of 3·$t^2$. Therefore, calculating two fiducial numbers for the interference during two quiet periods may be used to extrapolate an interference representing number for any particular period between these two quiet periods (or anywhere else; e.g., prior to the first quiet period and after the second quiet period) because the two fiducial numbers define a curve, and each interference that exists during other periods (e.g., during other quiets periods and during the alternating square signal) is expected to be on that curve. If Sw=$mT_t$ (e.g., if Sw=$T_t$, as demonstrated in FIG. 4C), the positive samples cancel out each other, and so do the negative samples. (In the former example, a positive sample is cancelled out by a corresponding/conjugated/in-phased negative sample.) In other words, if Sw=$mT_t$ and the interference's amplitude is constant, then by selecting a suitable sampling scheme (e.g., sampling frequency, number of samples, distance between samples, etc.), each positive sample either adds zero deviation or is cancelled out by another positive sample, and the same applies to the negative samples. The interference shown in FIG. 4C has a constant amplitude, 1.6v, that is centered with respect to, or biased to, the positive pulse 462 (with respect to the pulse's level +2.0v), and also with respect to, or biased to, the negative pulse 464 (with respect to the pulse's level −2.0v).

Time T1 can be shifted leftwards (e.g., earlier in time) or rightwards (e.g. later) within the cycle width of the square waveform (cycle width 470) as long as time T2 complies with the second sampling criteria; that is, T2 may remain in the same position relative to time T0, or it may move as well, to either direction, provided that the sampling gap, Sg, 460 includes n full cycles of the primary frequency of the interference signal, $f_t$, where n is an integer equal to or greater than 1.

Figure 4D:
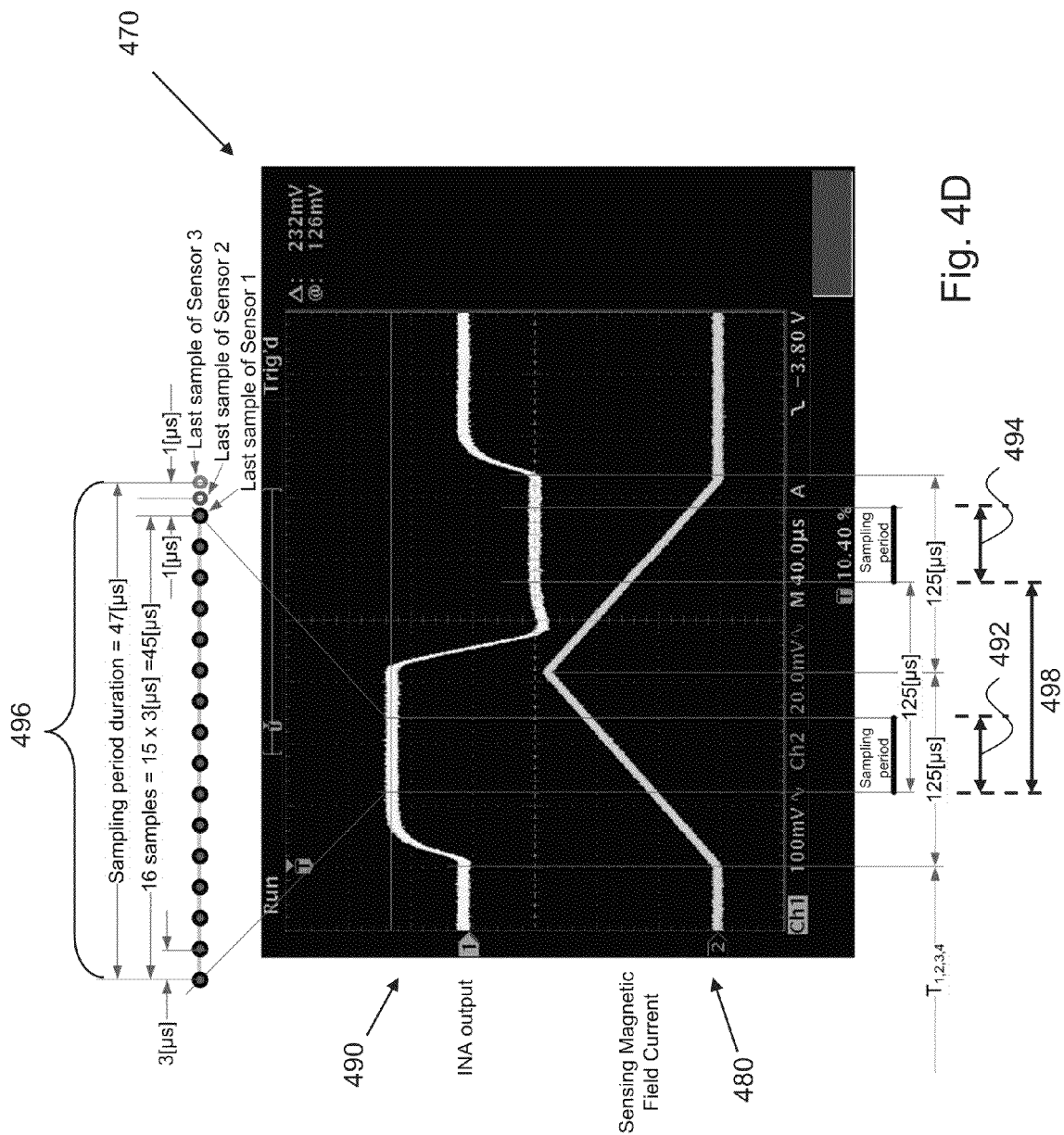
FIGS. 4D and 4E respectively depict an oscilloscope image and a graphical illustration thereof of a signal representing an example localization electromagnetic field, and an interference-free localization signal according to an embodiment of the invention.

FIG. 4D shows an oscilloscope display 470 displaying two signals 480 and 490 according to an example embodiment.

Figure 4E:
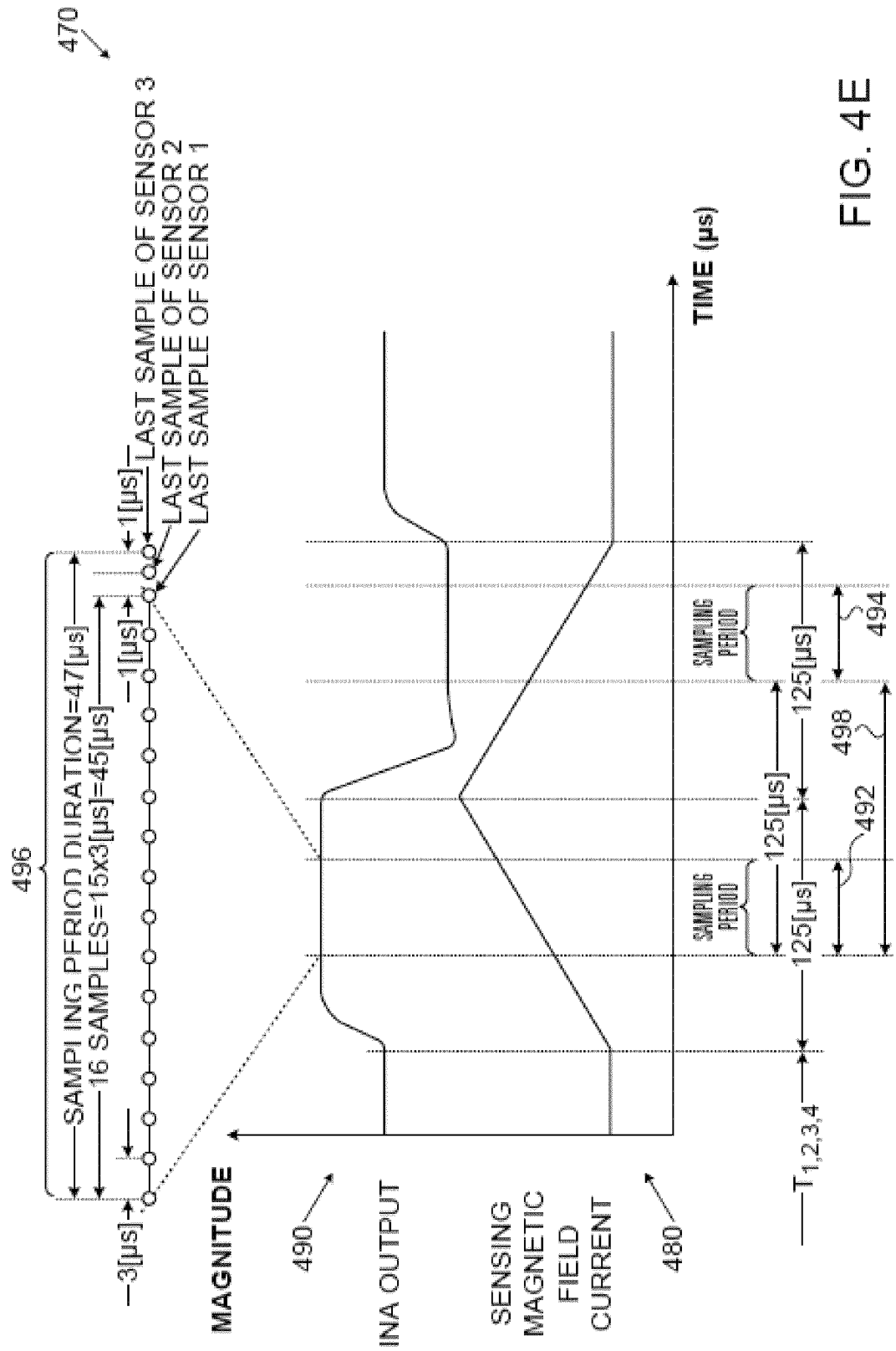

The signals shown are examples only; other signals may be used or produced. FIG. 4E is a graphical illustration of the image shown in FIG. 4D. Signal 480 is a localization electromagnetic field generated by localization signals source (LSS) 130 and sensed by (induced in) a sensing coil of the SCA. Signal 490, which is the EMF signal output by the sensing coil in response to signal 480, filtered using low pass filter ("LPF") and amplified, is an interference free localization signal. By way of example, the width of signals 480 and 490 is about 250 microseconds, which is equivalent to a frequency of 4 KHz. Sampling windows 492 and 494 are used to sample the positive pulse and the negative pulse, respectively, of signal 490. For clarity, sampling window 492 is shown zoomed-in (the zoomed-in samples are shown at 496). By way of example, each of sampling windows 492 and 494 is about 47 microseconds wide and includes 16 samples. Using a sampling frequency of 333 KHz, the sampling points are spaced 3 microseconds apart. In general, the interference induced in each sensing coil of the SCA can be described using mathematical expressions (3) to (6):

$$|B(\vec{r},t)| \cdot \hat{B}(\vec{r},t) \tag{3}$$

where B is the magnitude of the interference and $\hat{B}$ is the direction of the interference indicated by a uniform distribution random vector.

$$B = M(\vec{r},t) \cdot N(\vec{r},t) \tag{4}$$

where the term $M(\vec{r},t)$ is shown at expression (5):

$$M(\vec{r},t) = k(\vec{r}) + \sum_{i=1}^{\infty} \left[ A_i(\vec{r}) \cdot \cos(2\pi f_i \cdot t) + B_i(\vec{r}) \cdot \sin(2\pi f_i \cdot t) \right] \tag{5}$$

where $M(\vec{r},t)$ is periodic with respect to time t and has a cycle duration/width/length that is equal to the width of the sampling window, Sw (e.g., Sw 450 in FIG. 4C), divided by n, where n is an integer equal to or greater than 1; $f_1$ is the fundamental frequency of interference B; and $k(\vec{r})$ is a time-invariant component, and $N(\vec{r},t)$ is shown at expression (6):

$$N(\vec{r},t) = C_0(\vec{r}) + \sum_{i=1}^{\infty} C_i(\vec{r}) \cdot t^i \tag{6}$$

where $N(\vec{r},t)$ is a function that varies slowly relative to $M(\vec{r},t)$ with respect to time t (the fundamental frequency of $N(\vec{r},t)$ is typically several orders lower than that of $M(\vec{r},t)$), $C_0(\vec{r})$ is a time-invariant component, and the term $C_i(\vec{r}) \cdot t^i$ is time dependent component.

The multiplication of $M(\vec{r},t)$ and $N(\vec{r},t)$, as per equation (4), results in the four terms (7), (8), (9), and (10), which are shown below.

$$k(\vec{r}) \cdot C_0(\vec{r}) \tag{7}$$

$$C_0(\vec{r}) \cdot \sum_{i=1}^{\infty} \left[ A_i(\vec{r}) \cdot \cos(2\pi f_i \cdot t) + B_i(\vec{r}) \cdot \sin(2\pi f_i \cdot t) \right] \tag{8}$$

$$k(\vec{r}) \cdot \sum_{i=1}^{\infty} C_i(\vec{r}) \cdot t^i \tag{9}$$

$$\sum_{i=1}^{\infty} C_i(\vec{r}) \cdot t^i \cdot \sum_{i=1}^{\infty} \left[ A_i(\vec{r}) \cdot \cos(2\pi f_i \cdot t) + B_i(\vec{r}) \cdot \sin(2\pi f_i \cdot t) \right] \tag{10}$$

Since the aperiodic interference embodied in expression (7) is time invariant and the interferences embodied in expression (8) are periodic, these terms can be filtered out by applying equation (1) only on samples that are sampled during sensing periods. In other instances, such as for interferences that are embodied in expressions (9) and (10), equation (1) may be applied also on samples that are sampled during other periods than the sensing periods, for example it may be applied on samples that are sampled during one or more quiet periods. In general, a filtering process that is based on the application of equation (1) on samples, as explained herein and demonstrated, for example, in FIG. 4C, implements a simple and efficient filter because this filter is implemented using only basic mathematics (e.g., summation, subtraction).

Regarding expression (9), it describes time varying interferences ($k(\vec{r}) \cdot C_1(\vec{r}) \cdot t + k(\vec{r}) \cdot C_2(\vec{r}) \cdot t^2 +, \ldots$) that can be characterized, or quantified, during one or more quiet periods, and then filtered out by subtracting the interferences from the noisy localization signal resulting during each activation of the triangular localization signal.

In general, the number of the quiet periods that are required to characterize an interference element of expression (9) depends on the order of the interference element in expression (9). For example, one quiet period may suffice to characterize the first interference element of expression (9) ($k(\vec{r}) \cdot C_1(\vec{r}) \cdot t$) because the result of the application of equation (1) is an error that does not change over time and, therefore, one sampling thereof suffices; two quiet periods may suffice to characterize the second interference element of expression (9) ($k(\vec{r}) \cdot C_2(\vec{r}) \cdot t^2$) because the result of the application of equation (1) in this case is a linear error whose magnitude depends on time (t) and, therefore, two samplings thereof enable extrapolating interferences anywhere between these two sampling instances, for example during activation times (the time periods during which triangular localization signals are generated by LSS 130 and concurrently sensed by the SCA).

Setting the value of i to 1 in expression (10), the interference (see expression (11) below) may be cancelled out if the sampling gap Sg (e.g., Sg 460 in FIG. 4C) contains n cycles of the fundamental frequency of the interference ($Sg = nT_f$, where n is an integer equal to or greater than 1), and, in addition, the sampling window Sw (e.g., Sw 450 in FIG. 4C) also contains m cycles of the fundamental frequency of the interference (($Sw = mT_f$, where m is an integer equal to or greater than a predetermined number that may be, for example, 2).

$$C_i(\vec{r}) \cdot t \cdot [A_1(\vec{r}) \cdot \cos(2\pi f_1 \cdot t) + B_1(\vec{r}) \cdot \sin(2\pi f_1 \cdot t)] \tag{11}$$

Figure 4F:
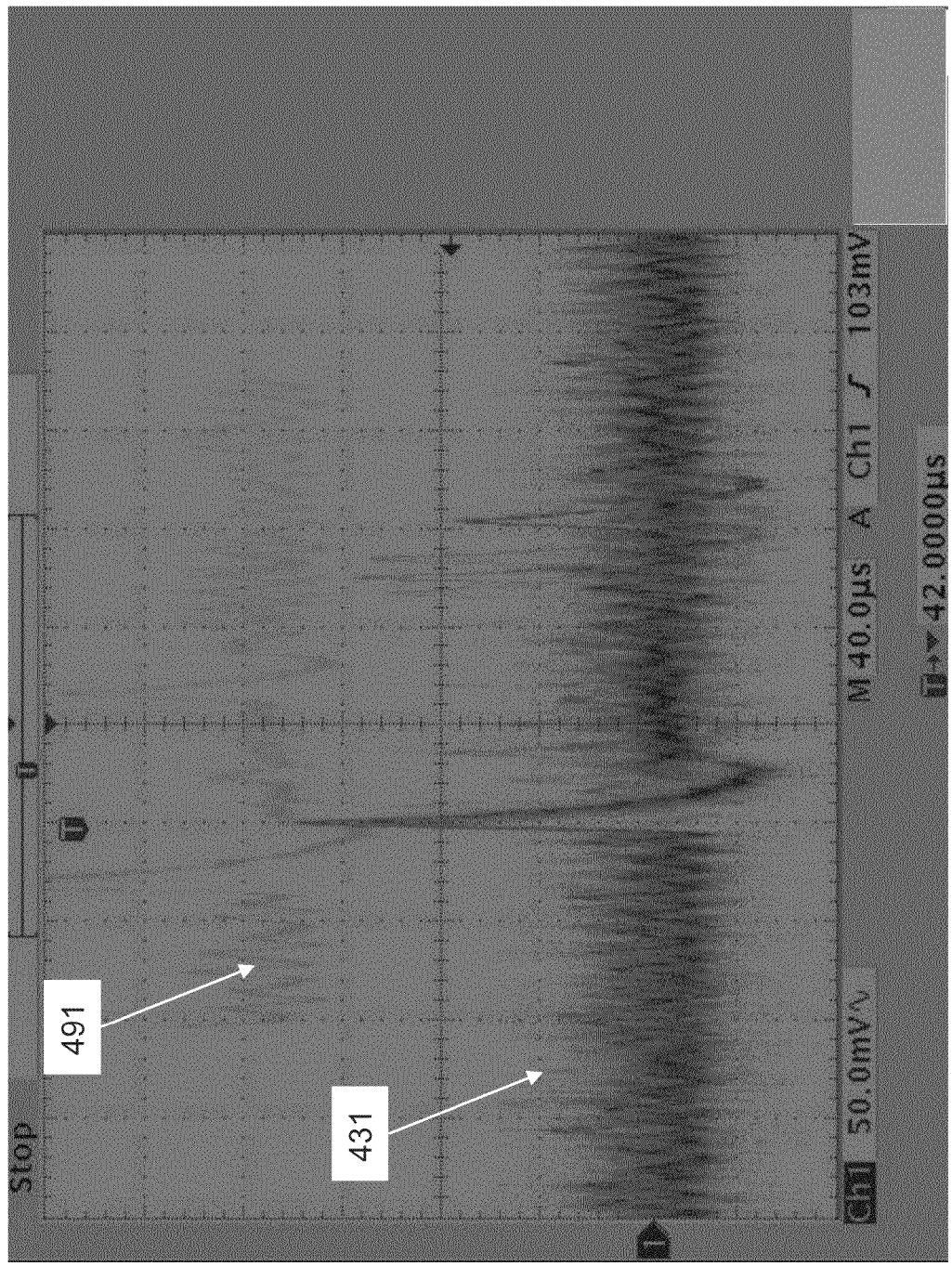
Figure 5A:
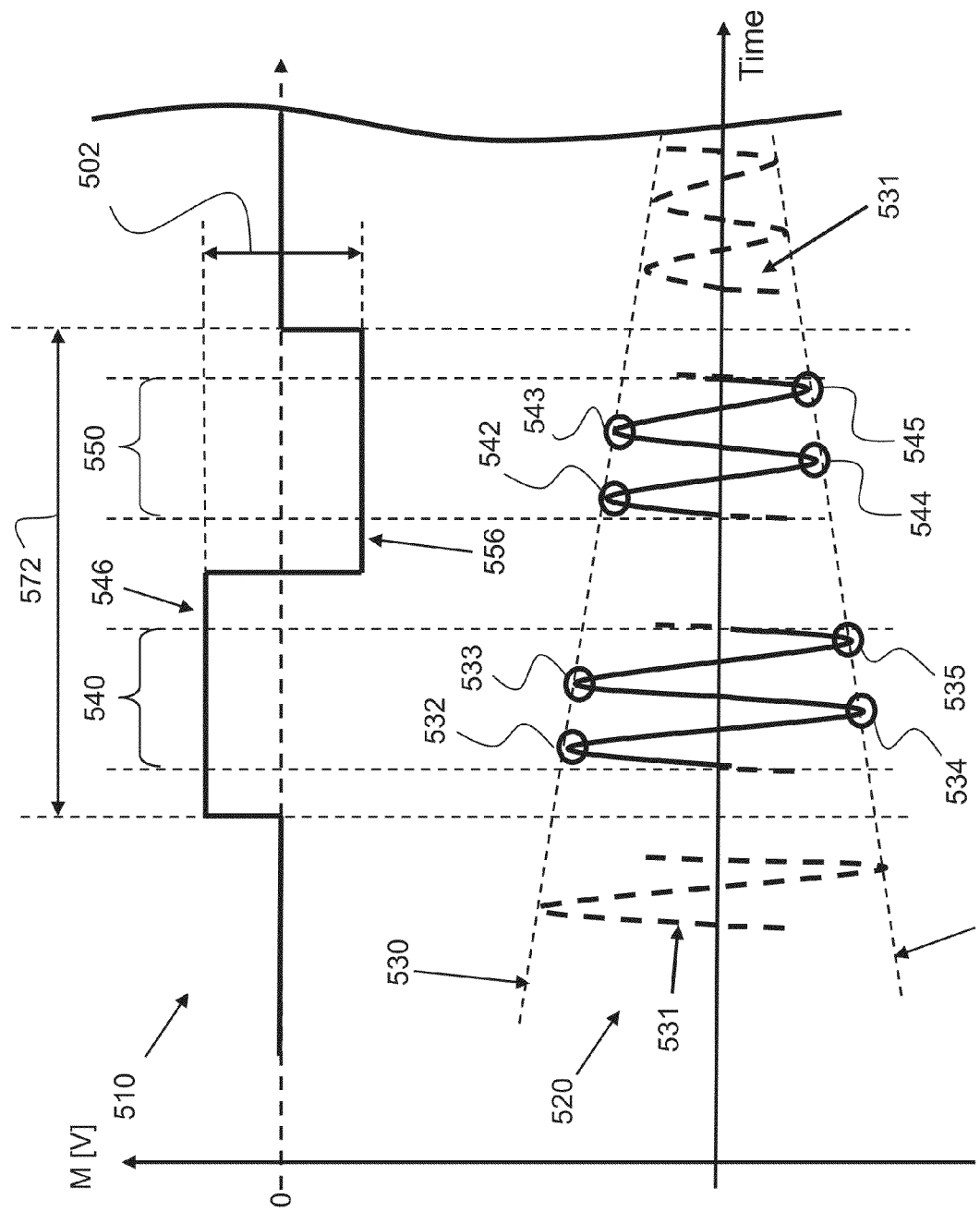
FIG. 5A schematically illustrates a square signal and a time variant interference signal according to an embodiment of the invention.
Figure 5B:
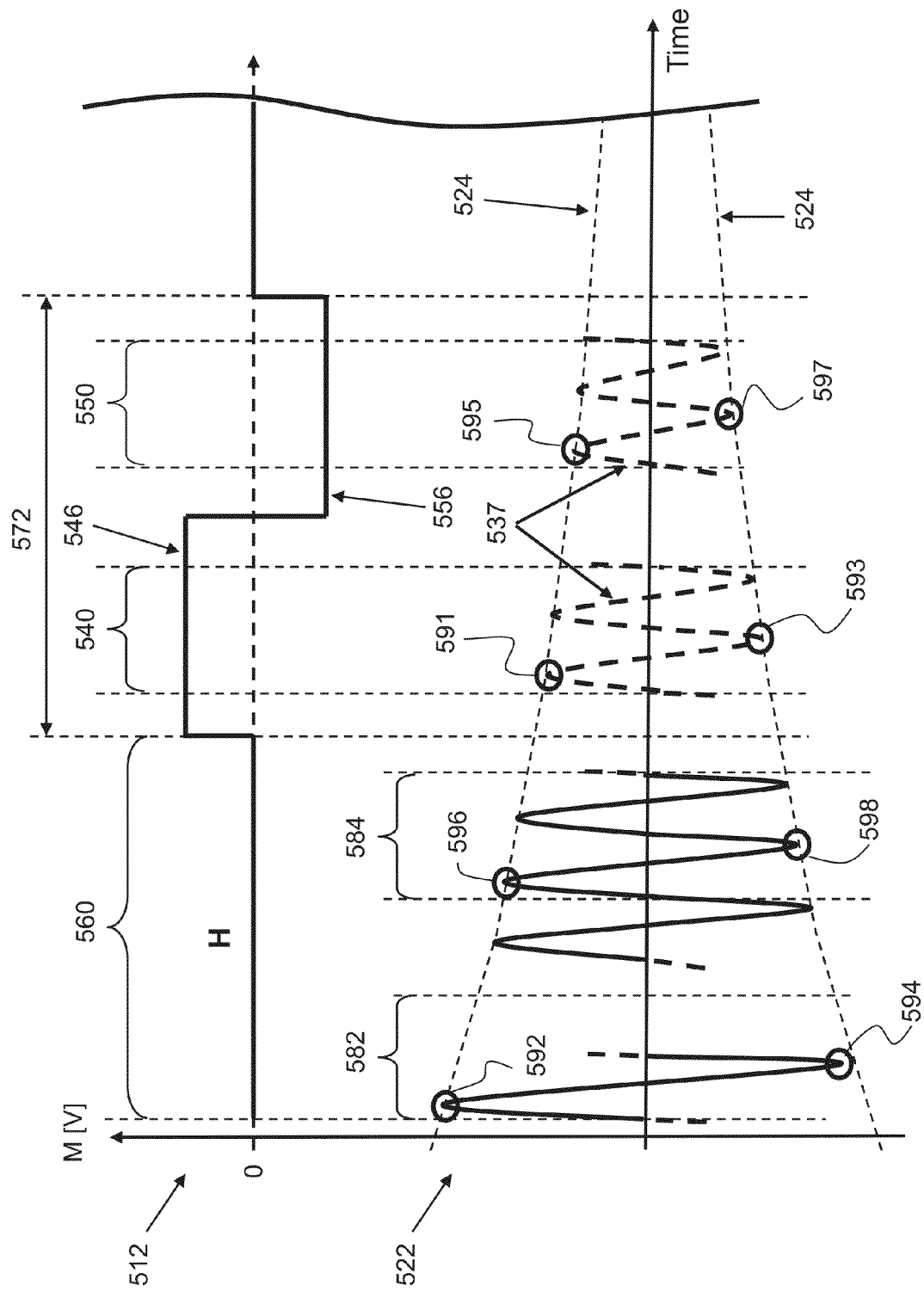
FIG. 5B schematically illustrates a square signal and a time variant interference signal according to an embodiment of the invention.

FIG. 4F shows simulation results of a noisy localization signal 491 and interference 431 according to an example embodiment. The signals shown are examples only; other signals may be used or produced. FIG. 4G is a graphical illustration of the image shown in FIG. 4F. As shown in FIG. 4F, the magnitude of interference 431 is very large comparing to the sensed localization signal 491. However, by using the filtering methods described herein, an interference free localization signal may be obtained, as demonstrated, for example, in FIG. 4C and in FIGS. 4D and 4E. The electromagnetic interference may be or include $n^{th}$-order interferences, where an '$n^{th}$-order interference' is an interference whose 'envelope' changes as a function of $t^n$, where t denotes time and n is a positive integer. For a zero-order interference and for a first-order interference, the error due to the interference samples, which is accumulated in a sampling window, is zero; for a second-order interference the error accumulated in a sampling window due to interference samples is a non-zero constant, for which reason it may be compensated for using one quiet period; for a third-order interference the error accumulated in a sampling window due to interference samples grows linearly, for which reason it may be compensated for using two quiet periods; for a fourth-order interference the error accumulated in a sampling window due to interference samples grows hyperbolically, for which reason it may be compensated for using three quiet periods, and so on. FIGS. 5A and 5B, which are described below demonstrate a first order interference and a second order interference, respectively.

As explained above and shown in expression (2), the electromagnetic interference caused by the maneuvering system (e.g., MMU 140) may include periodic components and aperiodic components. Determining on which samples equation (1) is to be applied may depend on the order of the interference up to which the interference is to be filtered. That is, depending on which periodic components and aperiodic components are to be filtered, equation (1) may be applied on samples sampled only during the sensing period, or on samples sampled during the sensing period and during one quiet period, or on samples sampled during the sensing period and during two quiet periods, or on samples sampled during the sensing period and during three quiet periods, and so on. As explained above, applying equation (1) on samples that are sampled during the sensing period cancels out the zero-order interference and the first-order interference, and the interferences caused by the higher order interferences during the sensing period may be extrapolated from higher order interferences that are sampled in one or more quiet periods.

The various conditions involved in the filtering of each type of interference, according to one embodiment, are summarized in table TABLE-1:

TABLE 1

| | | Conditions | | | |
|---|---|---|---|---|---|
| Inter. Order | Inter. Type | $Sw = mT_i$ | $Sg = nT_i$ (Gap between $Sw\_p$ and $Sw\_n$) | No. of Quiet Periods | Interference Serial Number |
| 0 | Periodic | No | Yes | 0 | (1) |
|   | Aperiodic | No | No | 0 | (2) |
| 1 | Periodic | Yes | Yes | 0 | (3) |
|   | Aperiodic | No | No | 1 | (4) |
| 2 | Periodic | Yes | Yes | 1 | (5) |
|   | Aperiodic | No | No | 2 | (6) |
| --- | | | | | |
| n | Periodic | Yes | Yes | n − 1 | |
|   | Aperiodic | No | No | n | |

Other conditions are possible. The conditions for filtering the various interference terms of expression (2) are described below for typical cases:

1. Zero-order interference: to cancel a zero-order interference, the width of the positive sampling window, $Sw\_p$ is identical to the width of the negative sampling window, $Sw\_n$. ("Positive sampling window" means the sampling window in the positive portion of the noisy localization signal; e.g., sampling window 450/1 in FIG. 4C, and "negative sampling window" means the sampling window in the negative portion of the noisy localization signal; e.g., sampling window 450/2 in FIG. 4C.) Since each positive sample that is sampled during the positive sampling window has a paired/in-phased negative sample that is sampled during the negative sampling window, in a first embodiment the sampling windows can have any width/duration (provided that the two sampling windows have the same width, and the samples are in phase with one another). In the first embodiment, cancellation of the interference is effected by cancelling each positive sample by a corresponding in-phased negative sample (the wider the sampling window, the more samples cancel each other). Satisfying the condition $Sg=nT_I$ facilitates 'cross-cancellation' of interference samples; that is, using the condition $Sg=nT_I$ enables selecting sampling points such that each positive sample is in phase with, and therefore cancelled by, a negative sample. Satisfying the condition $Sw=mT_I$ enables cancelling out various high-order periodic interferences. There is no need in one embodiment to sample the interference during any quiet period because the samples of the zero-order interference sampled during the sensing period are completely cancellable without requiring additional sampling such as sampling during a quiet period. The zero-order periodic interference may have two more options. That is, one of the conditions $Sw=mT_I$ and $Sg=nT_I$ may be met, or both conditions may be met.

2. First-order interference: as explained above, there is a first-order periodic interference, $K_1 t \cdot \cos(2\pi f \cdot t + \phi_1)$ (interference serial number 3 in TABLE-1) and a first-order aperiodic interference $C_1 \cdot t$ (interference serial number 4 in TABLE-1). In order to cancel the first-order periodic interference $K_1 t \cdot \cos(2\pi f \cdot t + \phi_1)$, in one embodiment the duration of the positive sampling window and the duration of the negative sampling window have to be the same, and each sampling window has to satisfy the two conditions (2.1) $Sw=mT_f$, and (2.2) $Sg=nT_f$. There is no need to sample the interference during any quiet period because the samples of the first-order periodic interference sampled during the sensing period are completely cancellable without requiring additional sampling such as sampling during a quiet period.

In order to cancel the first-order aperiodic interference $C_1 \cdot t$, the positive sampling window and the negative sampling window have to in one embodiment have the same duration, and the interference has to be quantified (e.g., by sampling it and applying equation (1) on the samples) during one quiet period for the reasons explained below. Because the aperiodic interference $C_1 \cdot t$ increases linearly as a function of time, the interference samples do not cancel out each other individually (by the sample). However, since the values of these samples grow linearly over time, the difference between the amplitudes of each two adjacent samples is constant. Therefore, each amplitude difference between two adjacent positive samples may be cancelled out by the amplitude difference between two adjacent negative samples. In other words, interference samples are cancelled out by the pairs, where a pair of positive samples cancel out a pair of negative samples (cross-cancellation is, therefore, used in this case as well). Therefore, the duration of the positive sampling window has to be identical to the duration of the negative sampling window.

3. Second-order interference: as explained above, there is a second-order periodic interference, $K_2 t^2 \cdot \cos(2\pi f \cdot t + \phi)$ (interference serial number 5 in TABLE-1) and a second-order aperiodic interference, $C_2 \cdot t^2$ (interference serial number 6 in TABLE-1). In order to cancel the second-order periodic interference $K_2 t^2 \cdot \cos(2\pi f \cdot t + \phi)$, the duration of the positive sampling window and the duration of the negative sampling window in one embodiment have to be the same, and each sampling window has to satisfy the two conditions (2.1) $Sw = mT_f$, and (2.2) $Sg = nT_f$. In addition, the interference in one embodiment has to be sampled during one quiet period. In order to cancel the second-order aperiodic interference $C_2 \cdot t^2$, the positive sampling window and the negative sampling window in one embodiment have to have the same duration, and the interference in one embodiment has to be sampled during two quiet periods.

FIG. 5A schematically illustrates a square signal 510 and a time variant interference signal 520 according to an example embodiment. Signal 510 and signal 520 are not drawn to scale (signal 520 is drawn excessively larger than signal 510 for clarity). Interference signal 520, which is an exemplary first-order periodic interference, decays/decreases linearly as a function of time (the 'envelope' of decaying signal 520 is shown at 530). Therefore, the interference sensed, for example, by each sensing coil of the SCA during positive sampling window (Sw) 540 of sensing period 572 and the interference sensed by the sensing coils during negative sampling window (Sw) 550 of sensing period 572 are different. For example, the magnitude, in average, of the interference sensed during sampling window (Sw) 540 is larger than the magnitude of the interference sensed during sampling window (Sw) 550. For example, interference magnitude 532 in Sw 540 is larger than magnitude 542 in Sw 550.

Because of the linearity of interference signal 520 (envelope 530 is linear), the difference between the absolute values of samples 532 and 534 is identical to the difference between the absolute values of samples 542 and 544. Since the first difference is superimposed on (biased to) the positive pulse 546 and the other difference is superimposed on (biased to) the negative pulse 556, applying equation (1) to samples 532, 534, 542, and 544 results in the 'positive' pair of samples (e.g., samples 532 and 534) and the 'negative' pair of samples (e.g., samples 542 and 544) cancelling out each other. Other positive (or negative) samples are likewise cancelled out by other negative (or positive) samples. In the example shown in FIG. 5A, no interference extrapolation is required because the interference samples that are sampled during sensing period 572 cancel out each other, thus leaving (after application of equation (1) on them) a number that represents the genuine magnitude 502 of localization signal 510.

In FIG. 4C, interference samples cancel each other on a sample-by-sample basis, meaning that each interference sample is cancelled by a paired interference sample that, subject to the sampling criteria/conditions specified herein, may be selected from the same sampling window, or from a different sampling window. (In general, the basic 'samples cancellation group' ("SCG") that is required to cancel zero-order interferences (of which FIG. 4C is an example) includes two samples. In contrast to FIG. 4C, in the example shown in FIG. 5A the basic samples cancellation group (SCG) that is required to cancel first-order interferences (of which FIG. 5A is an example) includes four samples. Group of interference samples 532, 534, 542, 544 and group of interference samples 533, 535, 543, and 545 are exemplary samples cancellation groups (SCGs). Signal portions 531 of interference signal 520 are distinctively shown in broken line to indicate that they are not sampled.

FIG. 5B schematically illustrates a square signal 512 and a time variant interference signal 522 according to another example embodiment. Signal 512 and signal 522 are not drawn to scale (signal 522 is drawn excessively larger than signal 512 for clarity). Interference signal 522 is an exemplary second-order periodic interference that decays/decreases as a function of time (the 'envelope' of decaying signal 522 is shown at 524). Since interference 522 is a second-order interference, the differences between the interference samples sensed by each sensing coil of the SCA during sampling window or period (Sw) 540 of sensing period 572 are different then the differences between the interference samples sensed by the sensing coils during sampling window or period (Sw) 550 of sensing window 572. Therefore, the sample differences originating from signal samples that are sampled during sampling windows 540 and 550 do not cancel out each other. For example, the difference between sample 591 and sample 593 in sampling window 540 is larger than the difference between sample 595 and sample 597 in sampling window 550 (this is because the convergence of envelope 524 gets more moderate as time passes). Therefore, cancelling a second-order interference may require factoring in additional samples, for example samples that were taken/sampled before and/or after sensing period 572 (e.g., during a quiet period 560), as described below.

Since the interference decay/decrease rate, which is the rate at which the amplitude of envelop 524 decreases in time, is constant, the interference expected during sampling windows 540 and 550 may be extrapolated, or inferred or deduced, from samples that are taken during a quiet period. In FIG. 5B, interference signal 522 is sampled during two sampling windows 582 and 584 in a quiet period 560 that precedes sensing period 572. In general, if an interference is to be quantized/estimated during a particular quiet period, the interference has to be sampled during two sampling windows within the particular quiet period.

Applying equation (1) on the samples taken during sampling windows 582 and 584 of quiet period 560 (e.g., on samples 592, 594, 596, 598 and on additional like samples) may result in a fiducial number, R2, that may represent the second-order interference signal 522. Since the interference decay/decrease rate is constant, as explained above, fiducial number R2 represents the interference at any point along envelope 524. Therefore, the fiducial number R2 also represents the interference that exists in sampling windows 540 and 550 of sensing window 572. Therefore, the zero-order interference, first-order interference and the second-order interference superimposed on signal 512 may be cancelled out by (i) applying equation (1) on samples that are taken during sampling windows 540 and 550, to thereby obtain a number, R, that represents the zero-order interference and first-order interference free signal 512, and (ii) subtracting the fiducial number R2 (the number representing the second-order interference signal 522) from the representative number R (the number representing the zero/first-order interference free signal 512), the subtraction result Q (Q=R-R2) being a number that represents either the genuine (interference-free) square signal, or the genuine square signal and some interferences of higher orders. (The higher the order of the interference, the lower its magnitude. Therefore, interferences of relatively high orders may not be sensed by the electromagnetic field sensors in the in-vivo device, which means there would be no need to waste resources for dealing with them.)

Sampling windows or periods 582 and 584 may respectively temporally comply with the sampling windows 540 and 550. That is, sampling windows 582 and 584 may also comply with the sampling criteria described herein (Sw=$mT_f$ and Sg=$nT_f$). Signal portions 537 of interference signal 522 cannot be sampled during sensing window 572 (because the signal during that period is the noisy localization signal), for which reason it is distinctively shown in broken line; instead, the interference is evaluated using other portions of the interference signal 522 that may be sampled, for example, during sampling windows 582 and 584. Since sampling windows 582 and 584 of quiet period 560 respectively function in the same way as sampling windows 540 and 550 of sensing window 572, they may also respectively be designated as 'positive sampling window' and 'negative sampling window' for consistency.

In general, for filtering an $n^{th}$-order interference (where n lower order interferences are discussed above), the fiducial number representing the interference during one or more quiet periods may be calculated, and a linear combination expression similar to linear combination expression (12) may be used to obtain the number representing the interference, or to extrapolate that number during or for any particular period between the quiet periods.

$$\sum_{i=1}^{n-1} D_i \cdot I_{QUIET\_PERIOD\_i} = I_{EXTRAPOLAION\_WINDOW} \quad (12)$$

where n≥2, n−1 is the number of quiet periods used, $D_i$ is a constant ascribed to quiet period number i that can be found or determined by using a matrix of interference measurements, $I_{QUIET\_PERIOD\_i}$ is a fiducial number representing an interference sampled during a quiet period i, and $I_{EXTRAPULATION\_WINDOW}$ is an extrapolated or deduced number that represents the interference or an evaluated interference that is expected within or during a sampling window or period, or during an extrapolation window, similar to sampling window 540 or sampling window 550.

A sampling window or period may also be referred to, or thought of, as an extrapolation window or period if the number representing the interference during that window is extrapolated or deduced. For example, time window 540 is a 'sampling window' because samples may be taken during this window to evaluate zero-order interference and first-order interference, and it may also be an 'extrapolation window' because numbers that represent a second-order interference and higher-order interferences may be extrapolated using samples that are taken during other time windows (e.g., during quiet period(s)).

Extrapolating a number that represents an interference in a particular time period characterizes the interference that is expected to exist in the particular time period. After the number that represents the interference is extrapolated for a particular extrapolation/sampling window (e.g., for extrapolation/sampling window 540), the interference may be removed (cancelled or filtered out) from the output signal of each sensing coil by using, for example, expression (13):

$$\hat{S}_{SENSING\_WINDOW} = S_{SENSING\_WINDOW} + I_{EXTRAPOLATION\_WINDOW} \quad (13)$$

where $\hat{S}_{SENSING\_WINDOW}$ is a number that represents the signal plus interference in a particular sampling window (e.g., sampling window 540) in the sensing window, and is calculated based on samples that are taken during the sampling window; $S_{SENSING\_WINDOW}$ is a number that represents an interference free signal (the genuine square signal) in the particular sampling window (e.g., sampling window 540), and is to be found; and $I_{EXTRAPOLATION\_WINDOW}$ is a number that represents the interference that is expected to exists during the particular sampling window (e.g., sampling window 540), and is extrapolated from other one or more numbers that respectively represent interferences during one or more quiet periods. (It is noted that $\hat{S}_{SENSING\_WINDOW}$ and $I_{EXTRAPOLATION\_WINDOW}$ may be calculated by applying equation (1) on the corresponding samples.)

The number that represents an interference free signal ($S_{SENSING\_WINDOW}$) may be found using expression (14):

$$S_{EXTRAPOLATION\_WINDOW} = \hat{S}_{EXTRAPOLATION\_WINDOW} - I_{EXTRAPOLATION\_WINDOW} \quad (14)$$

FIG. 6 shows a timing diagram 600 according to an exemplary embodiment. Signal 610 illustrates one work cycle 612 of in-vivo device 110. Work cycle 612 includes an off period 614 during which the in-vivo device does not transmit data, and an on period 616 during which the in-vivo device transmits data (e.g., image data, localization data, etc.)

Signal 620 includes a sensing window 622 that is allocated for or by the in-vivo device for sensing localization signals that may be generated, for example, by LSS 130. Sensing window 622 may also be used to sense an interference that is electromagnetically induced by MMU 140 in SCA 210. Sensing window 622 may, therefore, be functionally divided into, or include, two sensing periods: one sensing period, which is referred to herein as a 'quiet period', for sensing only noises, and another sensing period, which is referred to herein as a 'sampling period', for sensing localization signals through electromagnetic induction. Signal 630 is a reconstruction of signal 610. Reconstruction of signal 610 may be performed, for example, by data recorder 120 or by data recorder 208, for example, in order to facilitate synchronization between in-vivo device 110, LSS 130, and MMU 140.

Signal 640 includes a blanking command trigger 642. Blanking command trigger 642 may be transferred from data recorder 120 or from data recorder 208 to MMU 140 (for example as part of synchronization signal 144) in order to inactivate MMU 140. (As explained above, MMU 140 does not shut down its operation completely during blank periods, and "inactivation of MMU 140" means that MMU 140 enters a dormant or standby state in which it only decreases the intensity of the maneuvering electromagnetic field rather than stopping generating it.) Signal 650 shows the time periods during which the maneuvering coils of MMU 140 are active. Since there is some inertia involved in changing the electrical state of the maneuvering coils of MMU 140, there is a delay period 652 that precedes a blanking period 654. Although not shown in FIG. 6, the maneuvering coils of MMU 140 are not completely shut down; as explained above, they operate at minimal capacity during blanking periods.

Signal 660 includes a trigger pulse 662 that LSS 130 uses to operate/activate the localization coils in order to generate localization signals to localize in-vivo device 110. Signal 670 includes a time period 672 during which the localization signals generating coils of LSS 130 are active. As explained above, LSS 130 may, during activation period 672, generate an activation burst that may be identical or similar to activation burst 310 in FIG. 3A, or to activation burst 360 in FIG. 3B, or to activation burst 380 in FIG. 3C, or it may generate an activation burst that has a different pattern. As shown in FIG. 6, the localization signals generating coils, which may be referred to 'position and orientation coils', are activated during a time period 672 that coincides with sensing window 622.

Figure 7:
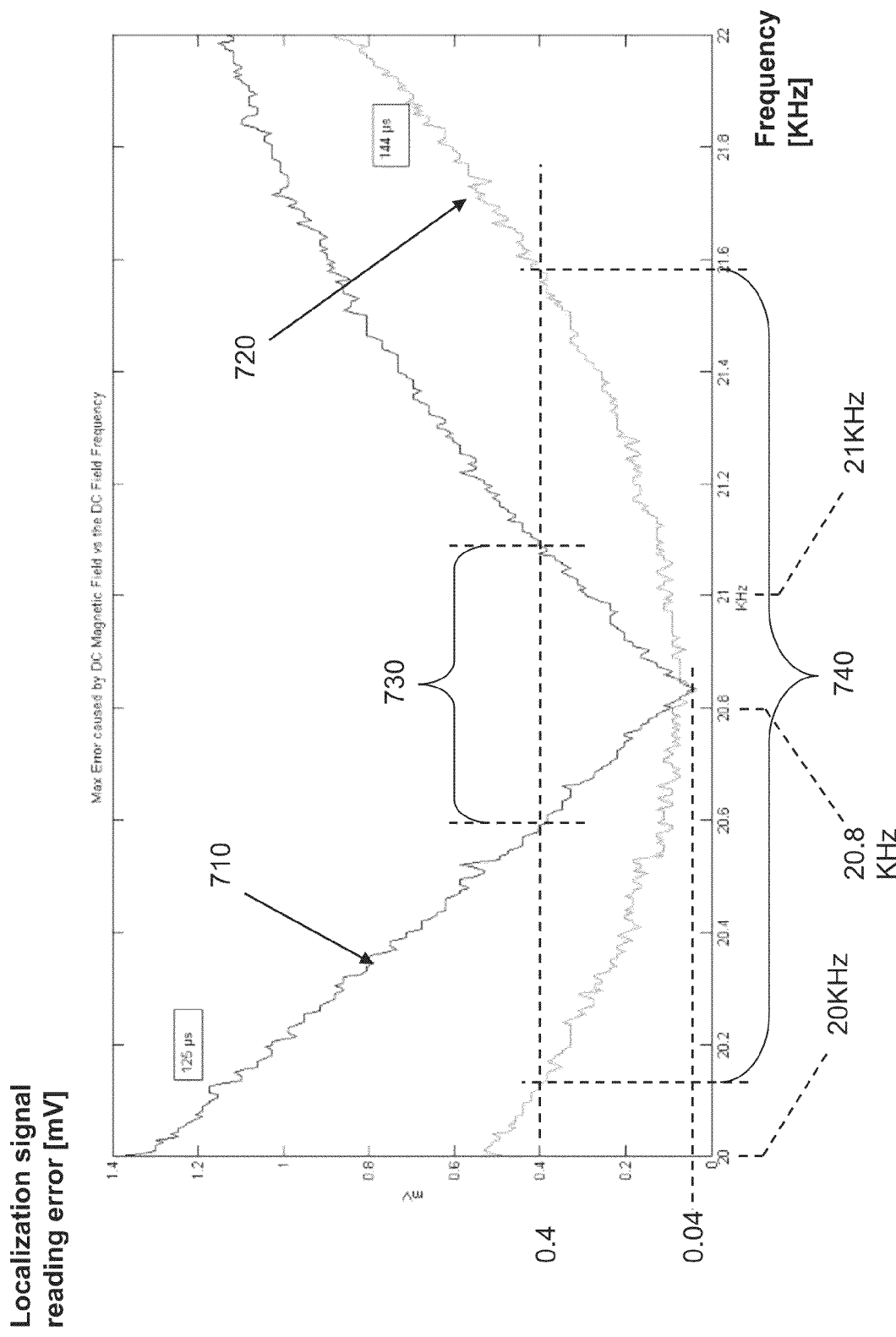
FIG. 7 is graph showing localization reading errors as a function of the fundamental frequency of the electromagnetic interference according to an embodiment of the invention.

FIG. 7 shows simulated graphs according to an example embodiment. The vertical axis (the ordinate, or y-axis) denotes the maximum position/orientation error caused by the maneuvering electromagnetic field/signal, and the horizontal axis (the abscissa, or x-axis) denotes the frequency of the maneuvering electromagnetic field/signal. Graph 710 and graph 720 refer to different sampling gaps, Sg, which resemble sampling gap, Sg, 460 in FIG. 4C. Graph 710 was obtained after setting the sampling gap, Sg, to 125 microseconds, sweeping through the frequency range of interest, for example through a frequency range that is centered at 20.8 KHz (e.g., sweeping through the frequency range 20 KHz through 22 KHz), and calculating the errors per the changed frequency. Likewise, graph 720 was obtained after setting the sampling gap, Sg, to 144 microseconds which is 3 interference periods (20.833 KHz interference period equal 48 μs), and calculating the errors per the changed frequency.

With the filtering methods (e.g., sampling criteria) described herein optimized for 20.833 KHz as the preferred frequency of the maneuvering electromagnetic field/signal, graph 710 shows that the maximum localization signal reading error is significantly low (about 0.04 mV) at 20.833 KHz. Other optimization frequencies may be used. Graph 710 also demonstrates that the localization signal reading error grows rapidly as the frequency of the maneuvering magnetic field/signal changes changed, which is an indication for the susceptibility (high sensitivity) of the filtration system to changes in the frequency of the maneuvering magnetic field/signal. Assuming that an error greater than 0.4 mV might be unacceptable for a specific application, the frequency range within which the frequency of the maneuvering magnetic field is permitted to vary (e.g., due to temperature changes) is rather limited (e.g., it is limited to a frequency range 730, which, in this example, is approximately 500 Hz). However, by setting the sampling gap to 144 microseconds, the frequency range within which the frequency of the maneuvering magnetic field is permitted to vary is extended (e.g., it is extended to a frequency range 740, which, in this example, is approximately 1.45 KHz), as graph 720 demonstrates. Graph 720 demonstrates that a filtering system that uses a sampling gap equal to 144 microseconds is much less susceptible to changes in the frequency of the maneuvering magnetic field than a system that uses a sampling gap equal to 125 microseconds. FIG. 7, therefore, demonstrates that the effect of the width of the sampling gap, Sg, may be determined, and its value may be controllably adjusted or manipulated to decrease the sensitivity of the filtrating process/system to the frequency of the maneuvering magnetic field. In other words, FIG. 7 demonstrates that the sensitivity of the filtrating process/system to the frequency of the maneuvering magnetic field can be controlled.

Figure 8:
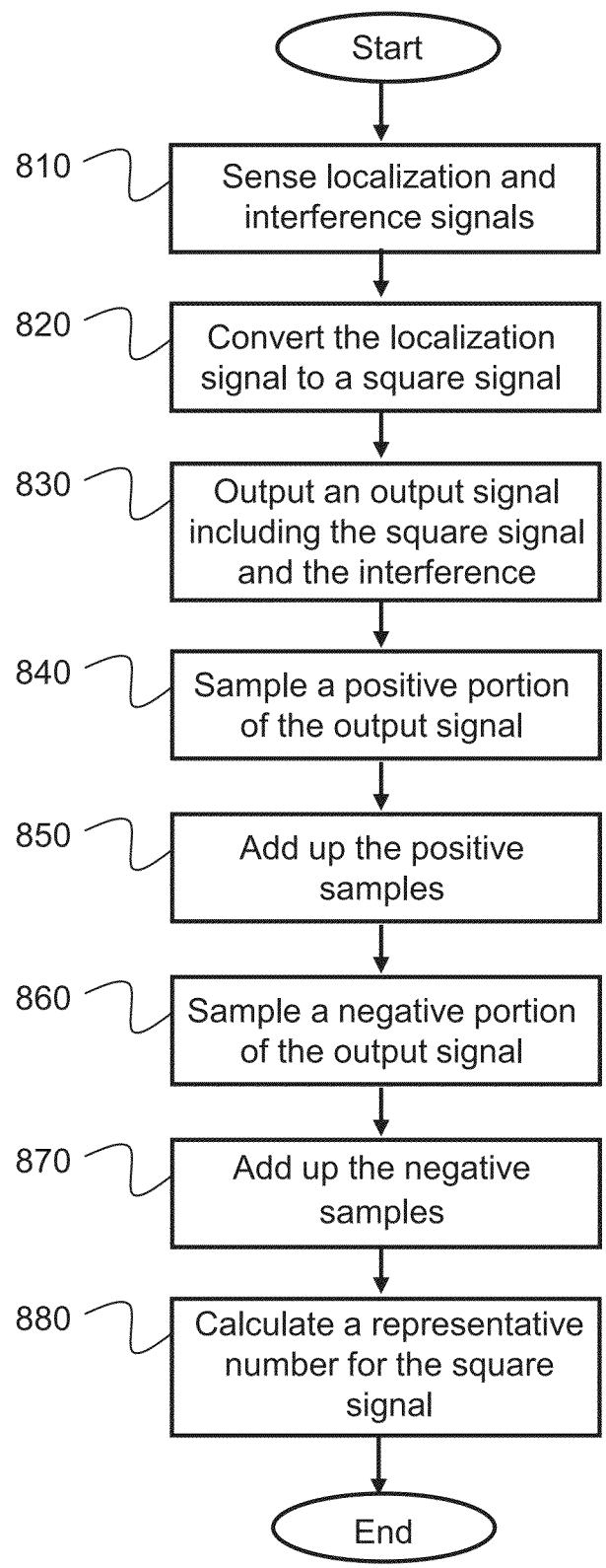
FIG. 8 is a flowchart of a method for cancelling out an electromagnetic interference in a localization signal without using quiet periods according to an embodiment of the invention.

FIG. 8 shows a method for cancelling out periodical interferences from a localization signal when both types of signals are induced in a sensing coil in an in-vivo device, according to an exemplary embodiment. At step 810, an electromagnetic localization signal burst and a periodic, and possibly aperiodic, electromagnetic interference signal may simultaneously be sensed by a sensing coil of a SCA (e.g., SCA 210) of an in-vivo device. The electromagnetic localization signal burst may include a series of n distinct triangular localization signals, where each triangular localization signal may have a duration $T_L$, and the periodic electromagnetic interference signal may have a fundamental cycle width $T_I$ that is very short comparing to $T_L$ (e.g., $T_I < T_L$; e.g. $2T_I < T_L$).

At step 820, which may be performed concurrently to step 810, each sensed triangular localization signal may be converted by the pertinent sensor to an alternating (e.g., square or square like) signal, for example as demonstrated in FIG. 4A. At step 830, the sensing coil may output an alternating output signal that includes both the alternating signal and the periodic (and possibly the aperiodic) electromagnetic interference signal superimposed on the alternating signal. Since the alternating signal is devised such that it has a positive level and a negative level, and the interference signal is superimposed on the alternating signal, the resulting noisy output signal also has a positive portion and a negative portion.

Starting at step 840, cancelling out the electromagnetic interference signal from the (noisy) alternating output signal may include sampling, using sampling specifics, a first portion of the alternating signal (e.g., in the positive portion of the alternating/output signal) during a first sampling window/period to obtain a first set of (e.g., positive) sample values (at step 840), calculating a first (e.g., positive) number, $N_P$, by adding up the first set of sample values (at step 850); sampling, using the sampling specifics, a second portion of the alternating signal (e.g., in the negative portion of the alternating/output signal) during a second sampling window/period to obtain a second set of (e.g., negative) sample values (at step 860); calculating a second (e.g., negative) number, $N_N$, by adding up the second set of sample values (at step 870), and, at step 880, calculating a representative number, $N_R$, for example by subtracting the second, or negative, number $N_N$ from the first, or positive, number $N_P$ (e.g., $N_R = N_P - N_N$). The representative number $N_R$ may represent, or indicate, the genuine (interference free) alternating signal, and thus it may reliably represent the location and/or orientation of the in-vivo device.

In one embodiment, at step 840, the first (e.g., positive) portion of the alternating (output) signal may be sampled at k sampling points in a first sampling window or period, Sw, thereby obtaining a first set of k (e.g., positive) sample values, wherein $Sw \geq mT_I$. At step 850, a first (e.g., positive) number, Np, may be calculated by adding up the first set of k (positive) sample values. At step 860, the second (e.g., negative) portion of the alternating (output) signal may be sampled at k sampling points in a second sampling window or period that has the same duration as the first sampling window or duration, to thereby obtain a second set of k (e.g., negative) sample values such that the first set of k (positive) sampling points and the second set of k (e.g., negative) sampling points are in phase with respect, or relative, to the phase of the periodic electromagnetic interference signal, and thus with respect to one another. At step 870, a second (e.g., negative number), Nn, may be calculated by adding up the second set of k (e.g., negative) sample values, and at step 880 the number, $N_R$, representing the alternating (output) signal with the interference cancelled out (e.g., the output signal including only, or mostly, the interference-free alternating (e.g., square) signal) may be calculated as described herein.

Since the fundamental frequency of the electromagnetic interference and/or the frequency, or the duration ($T_L$), of the localization signals may also change, the second sampling condition ($Sg = nT_I$) may no longer be met, in which case the efficiency of the filtering process as a whole may be degraded. This problem may be mitigated by adjusting the sampling scheme, or sampling specifics (e.g., number and/or locations of the k sampling points in the first/positive portion of the output signal and the number and/or locations of the k sampling points in the second/negative portion of the output signal, to accommodate for changes in $T_I$ and/or in the duration, $T_L$, of the localization signals. In order to facilitate the sampling timing adjustment, the frequency of the electromagnetic interference and the duration, $T_L$, of the localization signals may be monitored, for example occasionally or intermittently, and a determination regarding whether adjustments are required may be based on the result of the monitoring process.

Figure 10:
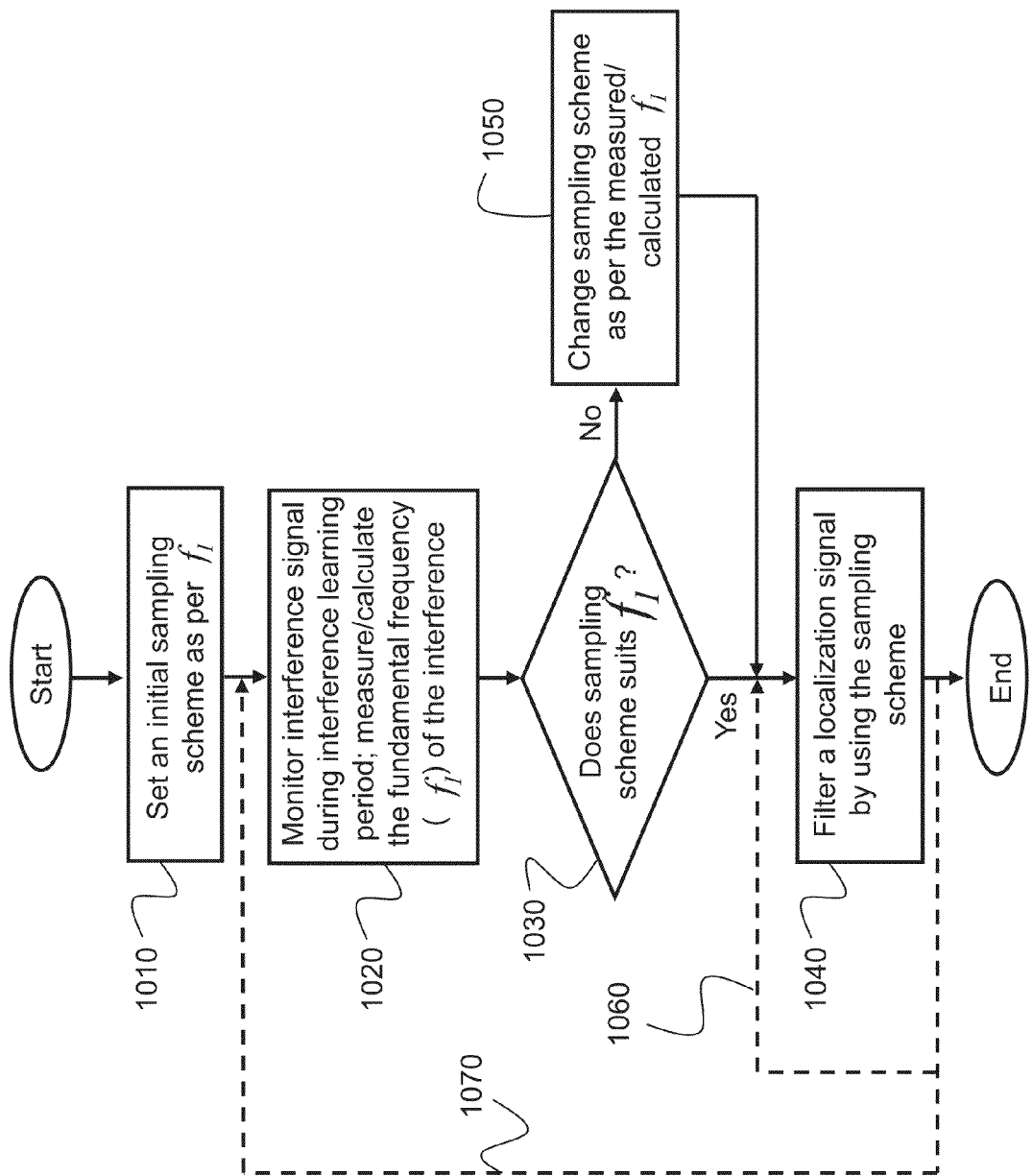
FIG. 10 is a flowchart of a method for adjusting sampling parameters according to an embodiment of the invention.

FIG. 8 shows a method for cancelling zero-order periodic and aperiodic interferences (as per interference serial numbers (1) and (2) in TABLE-1), and first-order periodic interference (as per interference serial number (3) in TABLE-1). As shown in TABLE-1, the interferences numbered (1), (2)

and (3) can be cancelled out without requiring evaluation of, or quantifying, interferences during quiet periods. A flowchart of a method for cancelling interferences (e.g., interferences numbered (4), (5), and so on, in TABLE-1) that include evaluation of, or quantifying, interferences during quiet periods is shown in FIG. 10, which is described below.

Figure 9:
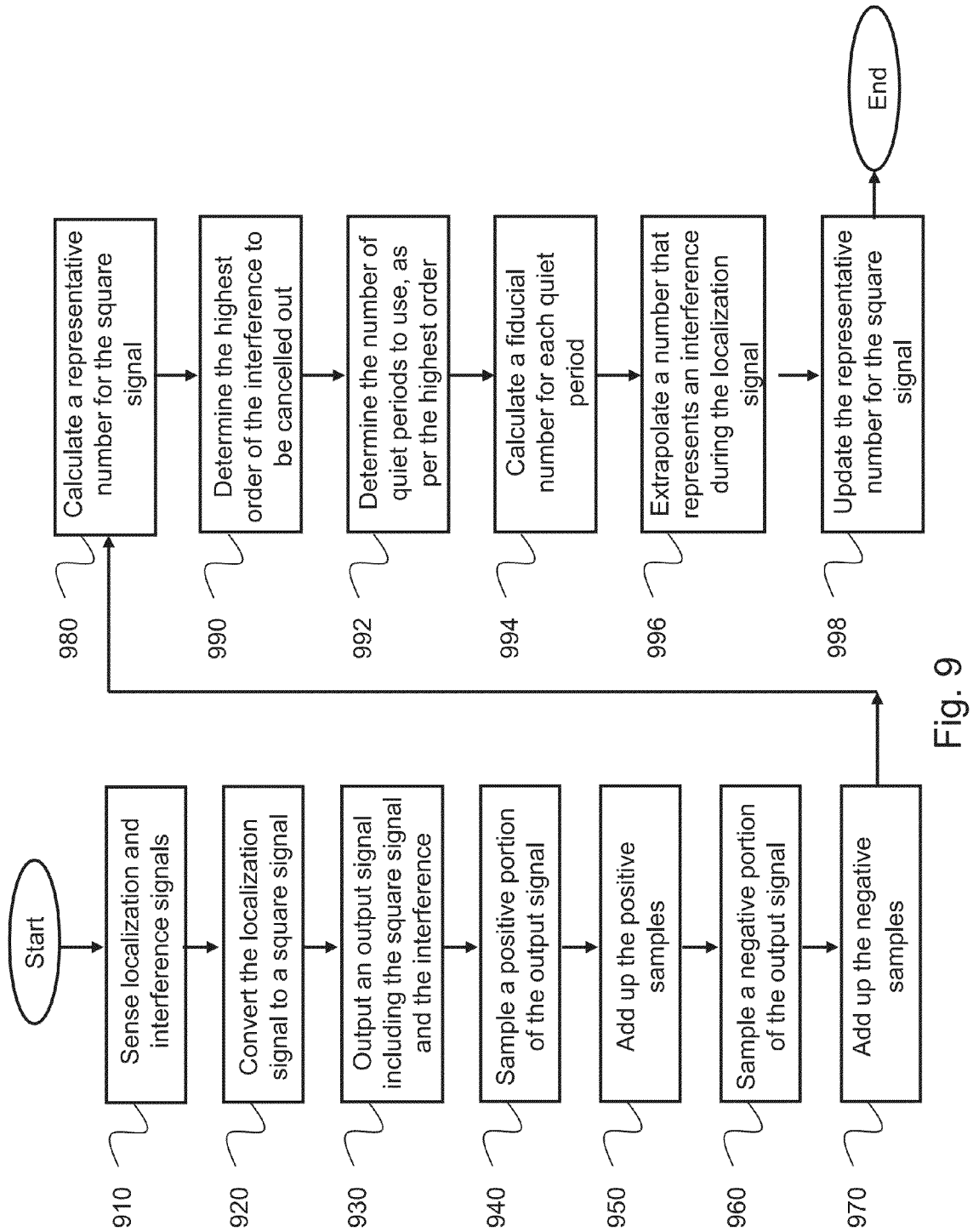
FIG. 9 is a flowchart of a method for cancelling out an electromagnetic interference in a localization signal by using also quiet periods according to an embodiment of the invention.

FIG. 9 is a flowchart of a method for cancelling interferences that require evaluation of, or quantifying, interferences during quiet periods. Steps 910, 920, 930, 940, 950, 960, 970 and 980 are respectively similar to steps 810, 820, 830, 840, 850, 860, 870 and 880 of FIG. 8. At step 990, the highest order of the interference to be filtered is determined, and, at step 992, the number of quiet periods corresponding to interference order and to the interference type is determined, for example using TABLE-1.

At step 994, fiducial numbers that represent, or that are derived from, the interferences during the quiet periods may be calculated, a fiducial number per quiet period, and, at step 996, a number that represents the interference during sensing of the localization signal by the in-vivo device may be extrapolated from the fiducial numbers.

For example, it may be determined, at step 990, that the highest order of the interference to be filtered is 2. As shown in Table-1, one quiet period may be required to cancel a second-order interference that is periodic, and two quiet periods may be required to cancel a second-order interference that is aperiodic. Continuing the example, at step 992 two quiet periods may be selected in order to filter interference up to the second-order aperiodic interference; at step 994 two fiducial numbers, which represent the interference during the two quiet periods may be calculated (one fiducial number for each quiet period); and, at step 996, the interference expected during sensing of the pertinent localization signal may be extrapolated from the two fiducial numbers. As explained above, the amplitude of a second-order interference is a function of $t^2$, and the fiducial numbers representing the interferences over time change a function of the derivative of $t^2$; that is, as a function of $2 \cdot t$. Therefore, the two fiducial numbers may be used to extrapolate a number for any particular period between the quiet periods, for example for the time during which the localization signals are sensed by the in-vivo device.

After the fiducial numbers are calculated (as per step 994) and a number representing the interference expected during sensing of the localization signal is extrapolated from them (as per step 996), at step 998 the number extrapolated from the fiducial numbers may be subtracted from the number calculated at step 980 to thereby enhance the interference filtering process because the number resulting from step 998 represents the square signal more accurately.

FIG. 10 is a flowchart of a method for adjusting an interference filtering scheme according to an embodiment. At step 1010, an initial sampling scheme is set as per a known, or expected, fundamental frequency, $f_I$, of the electromagnetic field interference. As explained above, the fundamental frequency, $f_I$ of the electromagnetic field interference may change within some margin, for example, due to different changes in the operating temperature of different components/units of the maneuvering system (e.g., MMU 140), tolerances of components of the maneuvering system, etc. Since the sampling specifics/conditions specified herein are tailored to the fundamental frequency of the electromagnetic field interference in order to optimize the interference filtering process, changes in the fundamental frequency, if ignored, may degrade the filtering optimization. Therefore, any of the sampling parameters that make up the sampling scheme, for example (i) the first, or positive, sampling window, Sw_p, (ii) the second, or negative, sampling window, Sw_n, (iii) the sampling gap (the time elapsing from the starting point of the first/positive sampling window and the starting point of the second/negative sampling window), (iv) the number of the sampling points in each sampling window, and (v) the sampling frequency, and any combination or subset of the sampling parameters, may be adjusted in order to optimize the filtering process to the actual fundamental frequency $f_I$, and, in general, to maintain optimization of the filtering process despite changes in the interference's fundamental frequency $f_I$.

At step 1020, the output signal of each sensing coil of the SCA, which may include an interference signal due to the maneuvering electromagnetic field generated by the maneuvering system, may be monitored during an interference learning period in order to measure or calculate the fundamental frequency $f_I$, and phase, of the interference signal. "An interference learning period" is a period during which no localization signal is transmitted, and only the maneuvering electromagnetic field is transmitted. A quiet period, which may be used to evaluate an interference, may also be, or used as, an interference learning period during which the fundamental frequency of the interference may be measured or calculated. Other time periods than quiet periods may be used as an interference learning period.

At step 1030 it is checked whether the currently set or used sampling scheme is optimized for the current, measured, or calculated fundamental frequency $f_I$. If the currently set or used sampling scheme is suitable/optimized for the current, measured, or calculated fundamental frequency $f_I$ (shown as "Yes" at step 1030), then, at step 1040, the first, or a next, localization signal may be filtered by using the initial sampling scheme. However, if the currently set, or currently used, sampling scheme does not suit the current, measured, or calculated fundamental frequency $f_I$ (shown as "No" at step 1030), for example because sampling specifics are not optimized for the measured/calculated fundamental frequency (e.g., because the actual/measured/calculated fundamental frequency differs from the expected, known, or previously measured/calculated frequency), then, at step 1050, one or more sampling specifics/parameters may be adjusted to optimize them to the actual/measured/calculated fundamental frequency. At step 1040, the first, or the next, localization signal may be filtered by using the adjusted sampling parameters.

A group of localization signals (e.g., one or more localization signal bursts) may undergo the interference filtering process by using the same sampling specifics/parameters (as shown at loop 1060), and the interference fundamental frequency may be measured/calculated once in a while or periodically in order to check whether a sampling parameter (e.g., sampling window, sampling gap, time locations and/or number of the sampling points, etc.) has to be adjusted, as shown at loop 1070. ("Once in a while" also means intermittently, occasionally, every $n^{th}$ localization signal burst, etc.).

Figure 11:
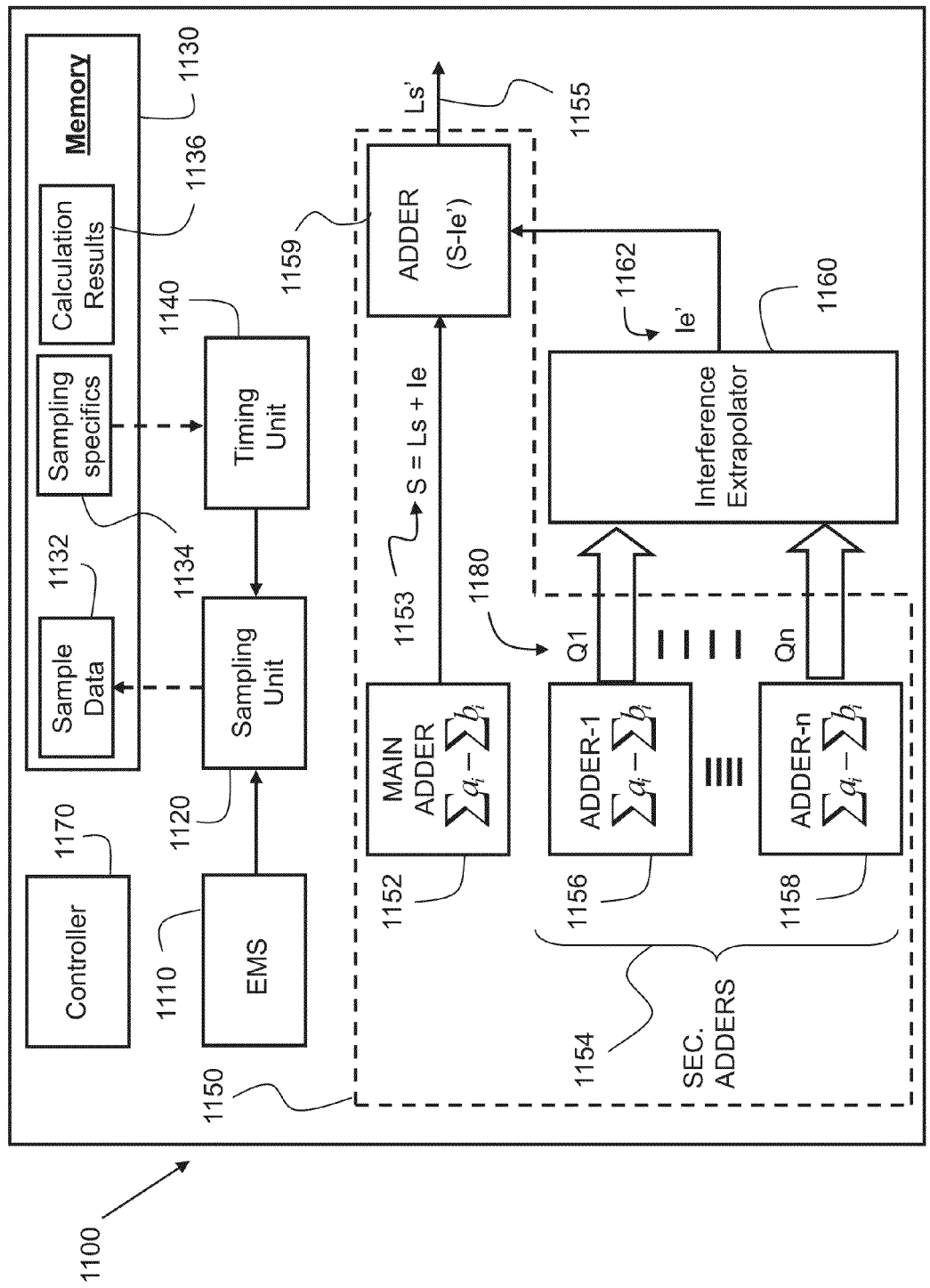
FIG. 11 is a block diagram of an in-vivo device according to an embodiment of the invention.

FIG. 11 shows a block diagram of an in-vivo device 1100 according to an embodiment. In-vivo device 1100 may include any component of FIG. 1 and FIG. 2, and vice versa, and components of FIG. 12 may fully or partly function like any component of any of FIGS. 1 and 2. In-vivo device 1100 may include an electromagnetic field sensor (EMS) 1110, a sampling unit 1120, a memory 1130, a timing unit 1140, an adders block 1150, an interference extrapolator 1160, and a controller 1170 that manages EMS 1110, sampling unit 1120, memory 1130, timing unit 1140, adders block 1150, and interference extrapolator 1160. Controller 1170, by executing software or instructions, may carry out steps which are performed by any one of sampling unit 1120, timing unit 1140, adders block 1150, interference extrapolator 1160, and other functions in in-vivo device 1100, and thus may function as these units.

EMS 1110 may include one or more electromagnetic field sensors (e.g., sensing coil(s)), for example three electromagnetic field sensors, or more than three electromagnetic field sensors, for sensing electromagnetic field signals. The one or more electromagnetic field sensors may be used to sense localization signals that are transmitted (e.g., by LSS 130) in the form of, for example, localization signals bursts. The one or more electromagnetic field sensors may also be used to monitor the electromagnetic field interference that is caused by the maneuvering electromagnetic field that is generated by the electromagnetic maneuvering system (e.g., MMU 140), for example during one or more quiet periods. Monitoring the electromagnetic field interference may enable measuring or calculating the fundamental frequency of the interference, and thus adjusting sampling parameters.

Sampling unit 1120 may sample the analog output signal that each electromagnetic field sensor outputs, and converts the analog sample values, or samples, into digital format. (The analog-to-digital converter is not shown in FIG. 11.) The digitized samples may be stored in memory 1130, for example as part of "sample data" 1232.

Controller 1170 may use timing unit 1140 to time operation of sampling unit 1120 according to, or based on, sampling specifics 1134 that are stored in memory 1130. Controller 1170, by using timing unit 1140 in conjunction with sampling unit 1120, may monitor electromagnetic field interferences in order to measure or calculate the fundamental frequency of the electromagnetic field interference. Controller 1170 may monitor the electromagnetic field interferences during an interference learning period that may be, for example, a quiet period.

Basing on the measured or calculated fundamental frequency, controller 1170 may determine whether any of sampling specifics 1134 has to be adjusted or not. Alternatively, controller 1170 may recalculate all the sampling specifics/parameters and replace sampling specifics/parameters that are stored in memory 1130 with the recalculated sampling specifics/parameters. Controller 1170 may occasionally (e.g., once in a while) check whether the current or actual sampling specifics/parameters are optimal for the actual, measured or calculated fundamental frequency of the interference, and if they are not, or if required, controller 1170 may change some of them or all of them. Controller 1170 may store interim calculation results in memory 1130, as part of "calculation results" 1136.

Adder block 1150 may include n+2 adders: an adder 1152, n adders 1154, which are designated as "ADDER-1" (shown at 1156), . . . , "ADDER-n" (shown at 1158), and another adder 1159. Adder 1152, which is referred to herein as the "main adder", may be used to calculate a number S (S is shown at 1153), whose value may represent (as per TABLE-1 above) a zero-order interference and first-order periodic interference free amplitude, Ls, of the sensed/induced localization signal, and first-order aperiodic interference and higher order interferences (e.g., second-order interference, third-order interference, and so on), Ie, that may be superimposed on the localization signal.

If the first-order periodic interference and higher order interferences, Is, are negligible, for example in comparison to the zero-order interference, main adder 1152 may suffice (no secondary adders may be required) because main adder 1152 cancels out the most influential electromagnetic field interferences (which are the zero-order interference and the first-order periodic interference). Assuming that the most influential electromagnetic field interferences are cancelled out by using only main adder 1152, the number S may represent the genuine localization signal with high proximity. However, as explained above, if an interference of a higher order (e.g., the second-order interference) is relatively strong, then, depending on the order of the interference up to which the interference is to be cancelled out, and depending also on whether the interference is periodic or aperiodic, one or more of adders 1154 may additionally be used to quantify the interference during, or for, one or more quiet periods (e.g., calculate a fiducial number for each quiet period). Adders 1150 are shown as distinct adders but, function-wise, one adder may perform the functions of some or all the adders.

Main adder 1152 adds up all the positive samples, $a_i$, of a localization signal and all the negative samples, $b_i$, of the localization signal, and subtracts the negative summing result from the positive summing result to obtain the number S (shown at 1153). Adders 1154, which are referred to herein as "secondary adders", function in the same way as main adder 1152 except that a secondary adder adds up 'positive' samples and 'negative' samples of the electromagnetic field interference that were sampled during a quiet period, and subtracts the negative summing result from the positive summing result to obtain a fiducial number Qi that represents, or quantifies, the interference during the quiet period number i. For example, ADDER-1 (shown at 1156) may use positive samples and negative samples that were sampled during a first quiet period to calculate a first fiducial number Q1 (shown at 1180) that represents, or quantifies, the interference during the first quiet period. Similarly, each of ADDER-2, ADDER-3, . . . , ADDER-n may use positive samples and negative samples that were sampled during the pertinent quiet period to calculate a fiducial number Qi (where i is an index that varies from 2 to n) that represents, or quantifies, the interference during the pertinent quiet period. If, for example, interferences up to (and including) the second-order interference are to be cancelled out, only main adder 1152 and one secondary adder (e.g., ADDER-1, shown at 1156) may be used. If, in another example, interferences up to (and including) the third-order interference are to be cancelled out, only main adder 1152 and two secondary adders (e.g., ADDER-1, shown at 1156, and ADDER-2) may be used.

Depending on the number of used quiet periods, the same number of adders may be selected from secondary adders 1154, and each selected secondary adder may output a fiducial number Qi for the pertinent quiet period. Interference extrapolator 1160, based on the set/determined highest interference order, may extrapolate a number Ie' (shown at 1162) from the fiducial numbers Qi, that represents various interferences that are expected to be superimposed on the localization signal. Adder 1159, then, subtracts Ie' from S in order to cancel these interferences out from S, and outputs 1155 a number, Ls', that represents the genuine localization signal with high accuracy.

Ie represents all the higher order interferences ("higher order" means second-order and higher orders) that may be superimposed on the localization signal, and Ie' represents some of the higher order interferences that may be superimposed on the localization signal. Therefore, subtracting Ie' from S (S−Ie'=Ls') may result in erroneous localization signal, Ls'=Ls+E, where E=Ie−Ie', where E is referred to herein as an "interference cancelling error". As explained above, main adder 1152 cancels out the most influential interferences, which means that Ie is typically very low in comparison to the localization signals source. Therefore, Ls' represents the genuine localization signal with high accuracy. The accuracy may be enhanced by using more quiet periods: the greater the number of the used quiet periods, the smaller the interference cancelling error, E. In-vivo device 1100 may translate the number Ls', and other like numbers that were obtained using other electromagnetic field sensors, to corresponding localization data, or it may transfer the number Ls', and additional similar numbers, to an external receiver or system (e.g., receiver 120 or 208).

Figure 12:
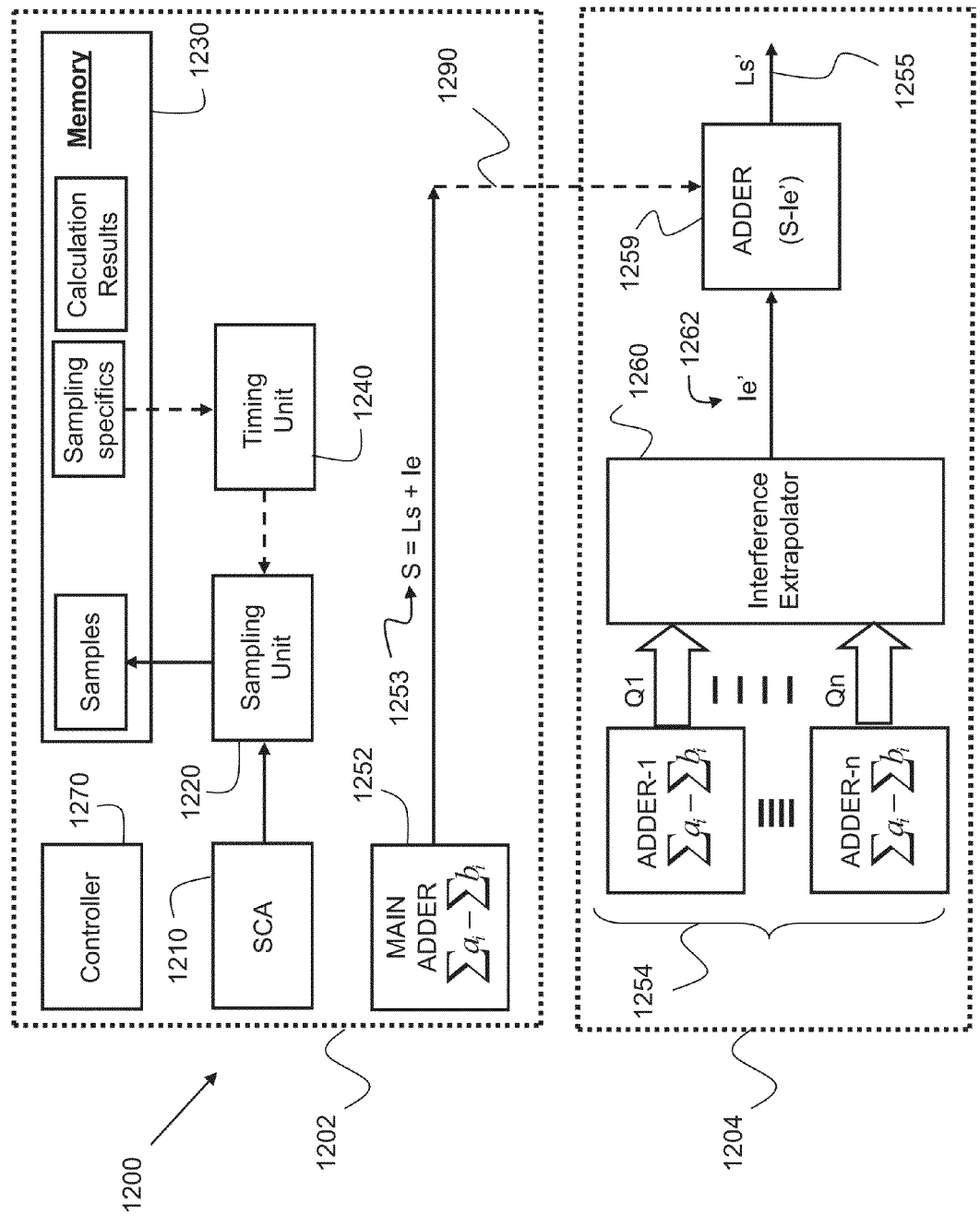
FIG. 12 is a block diagram of an in-vivo system according to an embodiment of the invention.

FIG. 12 shows a block diagram of an in-vivo system 1200 according to an embodiment. In-vivo system 1200 may include an in-vivo device 1202, and a receiver, or data recorder 1204, and the various functions and operations that are described in connection with FIG. 12 may be distributed between them. In-vivo device 1202 may be identical or similar to in-vivo device 110 in FIG. 1, or to in-vivo device 206 in FIG. 2, and may function in the same or similar way as any of them and as in-vivo device 1100 in FIG. 11. Receiver, or data recorder, 1204 may be identical or similar to receiver, or data recorder, 120 in FIG. 1, or to receiver, or data recorder, 208 in FIG. 2, and may function in the same or similar way as any of them and as described in connection with FIG. 11, which is described above.

In-vivo device 1202 may include a SCA 1210 that functions in the same or similar way as SCA 1110; a sampling unit 1220 that functions in the same or similar way as sampling unit 1120; a memory 1230 that functions in the same or similar way as memory 1130; a timing unit 1240 that functions in the same or similar way as timing unit 1140; main adder 1252 that functions in the same or similar way as main adder 1152; and controller 1270 that functions in the same or similar way as controller 1170.

Controller 1270 may operate SCA 1210, sampling unit 1220, memory 1230, timing unit 1240, and main adder 1252 to calculate the number S (shown at 1353). Then, controller 1270 may transfer 1290 the number S (e.g., in an image frame, or during a work cycle of the in-vivo device) to receiver 1204. Being in synchronization with in-vivo device 1202, receiver 1204 may monitor the electromagnetic field interference during a required/determined number of quiet periods, and select secondary adders, from secondary adders 1254, to respectively calculate fiducial numbers for the quiet periods. Then, interference extrapolator 1260 and adder 1259 may operate as described above in connection with interference extrapolator 1160 and adder 1159 in order to calculate Ls'. Receiver 1204 may translate Ls', and similar numbers that in-vivo device 1202 calculates by using other electromagnetic field sensors and transferred to receiver 1204, to corresponding localization data. Alternatively, receiver 1204 may transfer, or relay, the number Ls' and the other similar numbers to another system (e.g., as feedback; e.g., to MMU 140 and/or to LSS 130) to perform the translation.

Figure 13:
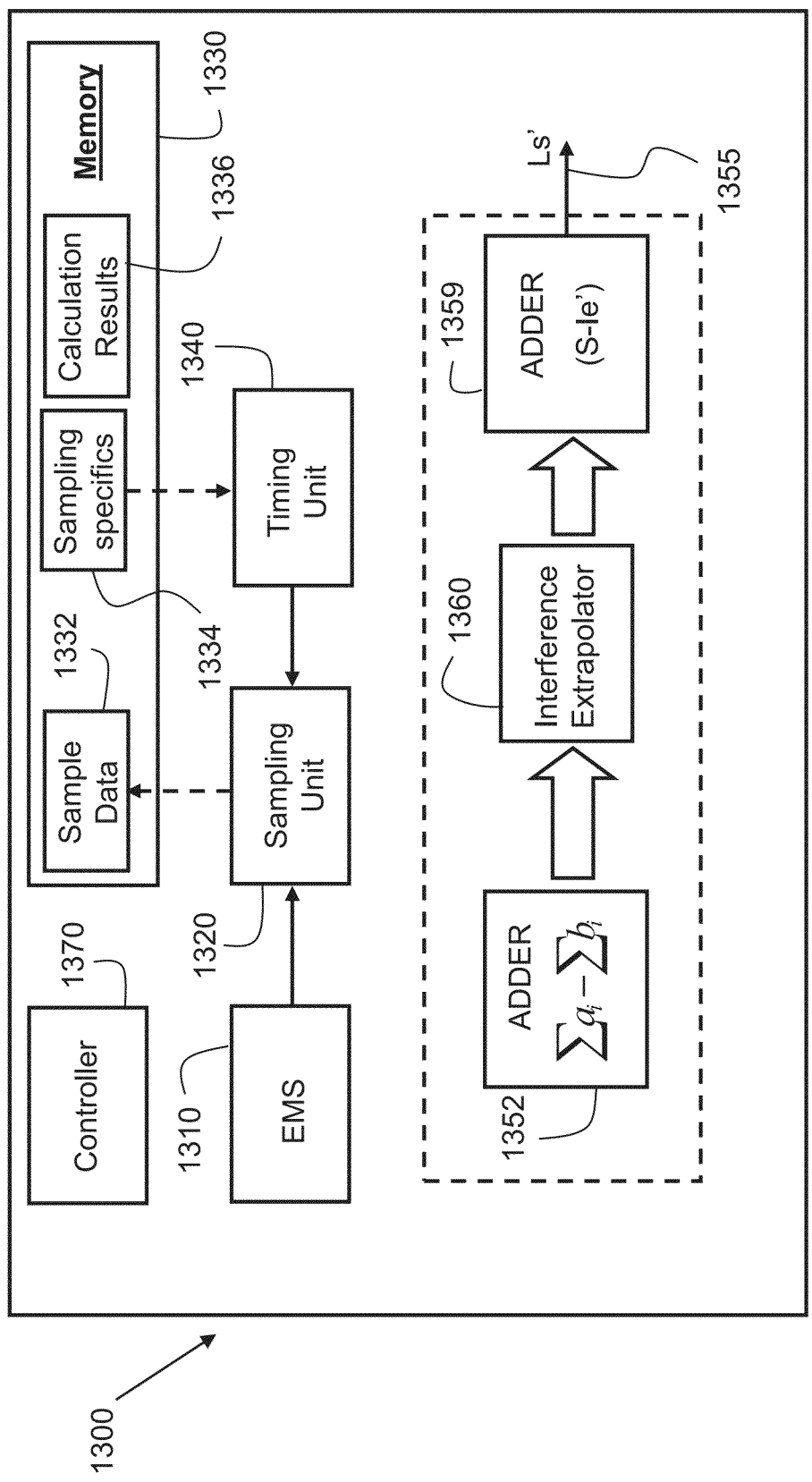
FIG. 13 is a block diagram of an in-vivo device according to an embodiment of the invention.

FIG. 13 is a block diagram of an in-vivo device 1300 according to another embodiment of the invention. In-vivo device 1300 may include a EMS/SCA 1310 that functions in the same or similar way as EMS/SCA 1110; a sampling unit 1320 that functions in the same or similar way as sampling unit 1120; a memory 1330 that functions in the same or similar way as memory 1130; a timing unit 1340 that functions in the same or similar way as timing unit 1140; an adder 1352 that functions in the same or similar way as main adder 1152 and as secondary adders 1154; and controller 1370 that functions in the same or similar way as controller 1170.

Controller 1370 may operate SCA 1310, sampling unit 1320, memory 1330, timing unit 1340, and adder 1352 to calculate and output a number for each time period during which the interference is evaluated/quantified. For example, if no quiet periods are used, samples may be taken only from the noisy localization signal sensed by EMS 1310, and adder 1352 may calculate only a number that represents, or quantifies the interference only during that time. In another example, if two quiet periods are used, one quiet period that precedes the localization signal and another quiet period that succeeds it, samples of the interference may be taken from the first quiet period, a corresponding fiducial number may be calculated by adder 1352 for the first quiet period and stored (e.g., in memory 1330; e.g., as part of calculation results 1336); then, a number may likewise be calculated for the noisy localization signal and stored in memory 1330; then a second fiducial number may likewise be calculated for the second quiet period and stored in memory 1330. Then, control 1370, in conjunction with interference extrapolator 1360, may extrapolate a number for the interference expected during the sensing of the localization signal from the two fiducial numbers, and, in conjunction with adder 1359, subtract the extrapolated number from the number representing the noisy localization signal, to thereby obtain an interference free localization signal 1355.

Figure 14:
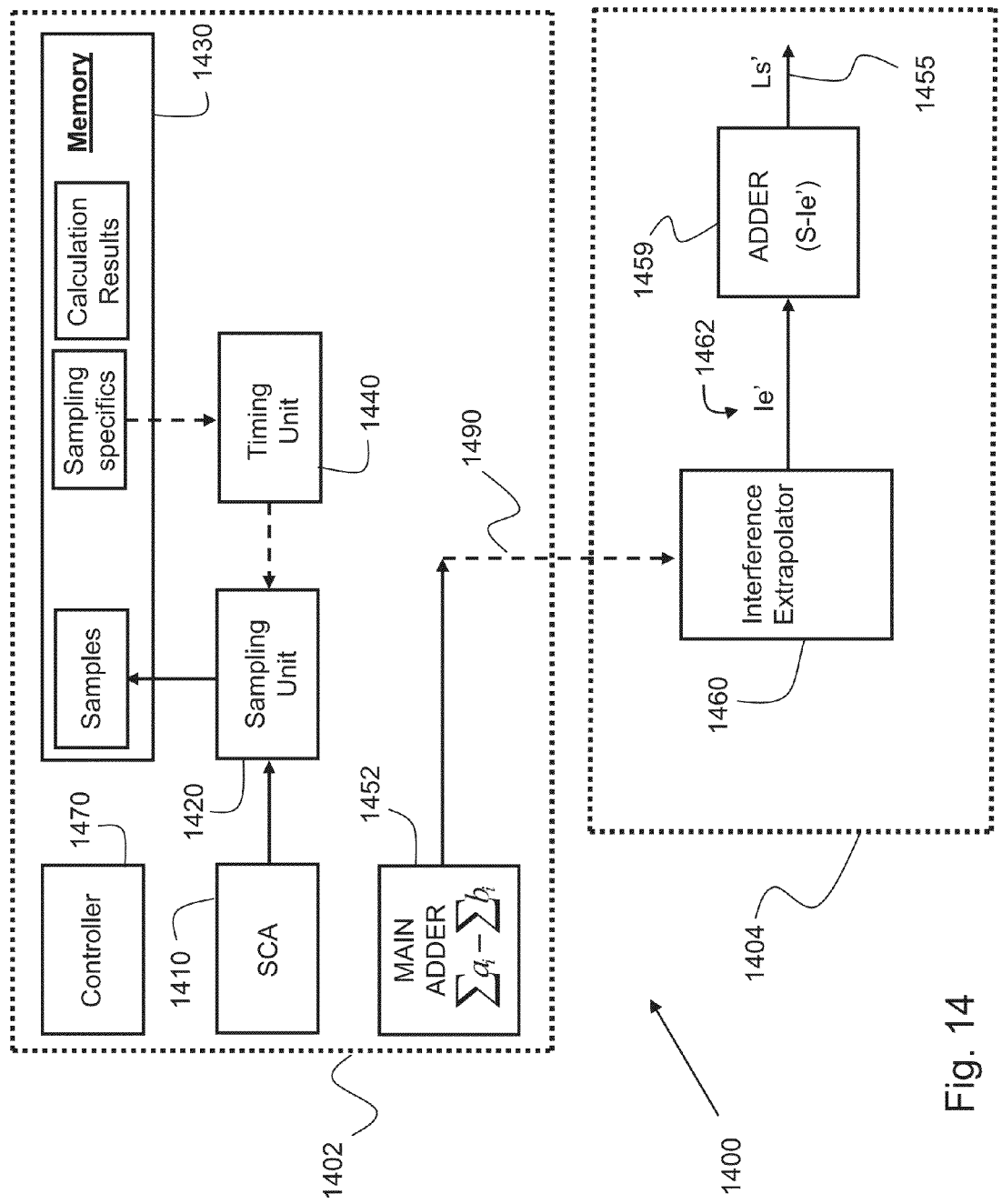
FIG. 14 is a block diagram of an in-vivo system according to an embodiment of the invention.

FIG. 14 is a block diagram of an in-vivo system 1400 according to another embodiment of the invention. In-vivo system 1400 may include an in-vivo device 1402, and a receiver, or data recorder 1404. In-vivo device 1402 may be identical or similar to in-vivo device 110 in FIG. 1, or to in-vivo device 206 in FIG. 2, and may function in the same or similar way as any of them and as in-vivo device 1100 in FIG. 11. Receiver, or data recorder, 1404 may be identical or similar to receiver, or data recorder, 120 in FIG. 1, or to receiver, or data recorder, 208 in FIG. 2, and may function in the same or similar way as any of them and as described in connection with FIG. 11, which is described above.

In-vivo device 1402 may include a SCA 1410 that functions in the same or similar way as EMS/SCA 1110; a sampling unit 1420 that functions in the same or similar way as sampling unit 1120; a memory 1430 that functions in the same or similar way as memory 1130; a timing unit 1440 that functions in the same or similar way as timing unit 1140; main adder 1452 that functions in the same or similar way as main adder 1152; and controller 1470 that functions in the same or similar way as controller 1170. In-vivo device 1402 may function in the same way as in-vivo device 1300, except that in-vivo device 1402 may calculate the required representative numbers (e.g., fiducial numbers and numbers representing or quantifying interferences during localization signals) by using main adder 1452, and transfer these numbers to receiver 1404. Receiver 1404 may temporarily store these numbers, extrapolate a number 1462 from fiducial number(s) by using interference extrapolator 1460, and use adder 1459 to subtract the extrapolated number from the number representing the noisy localization signal (which is also transferred from in-vivo device 1402), to thereby calculate a substantially interference free localization signal Ls' (shown at 1455). Receiver 1404 may translate the number Ls', and similar numbers that in-vivo device 1402 calculated by using other electromagnetic field sensors and transferred to receiver 1404, to corresponding localization data. Alternatively, receiver 1404 may transfer, or relay, the number Ls' and the other similar numbers to another system (e.g., as feedback; e.g., to MMU 140 and/or to LSS 130).

The alternating square signal referred to herein is only an example, and the methods disclosed herein are likewise applicable to other types of alternating signals that may generally be square. For example, the methods may be applicable to signals that have discernible positive portion and negative portion whose magnitudes do not change significantly (i.e., their magnitude may change within relatively small margin), or they change relatively slowly. Referring to an ideal square signal (e.g., FIGS. 4A, 5A, 5B) simplifies the understanding of the interferences cancelling methods.

The interference described herein does not necessarily have to originate from a switching frequency of a pulse width modulation (PWM) circuit; it can originate from other sources as well. That is, the methods for cancelling out interferences may likewise be applicable to any periodic interference, regardless of its origin, because the sampling scheme can be adjust to the sole frequency, or to the fundamental frequency, of the interference.

The articles "a" and "an" are used herein to refer to one or to more than one (e.g., to at least one) of the grammatical object of the article, depending on the context. By way of example, depending on the context, "an element" can mean one element or more than one element. The term "including" is used herein to mean, and is used interchangeably with, the phrase "including but not limited to". The terms "or" and "and" are used herein to mean, and are used interchangeably with, the term "and/or," unless context clearly indicates otherwise. The term "such as" is used herein to mean, and is used interchangeably, with the phrase "such as but not limited to".

Different embodiments are disclosed herein. Features of certain embodiments may be combined with features of other embodiments; thus certain embodiments may be combinations of features of other or multiple embodiments. Embodiments of the invention may include an article such as a computer or processor non-transitory storage medium, such as for example a memory, a disk drive, or a USB flash memory, encoding, including or storing instructions, e.g., computer-executable instructions, which when executed by a processor or controller, carry out methods disclosed herein. For example, a system may include a non-transitory storage medium such as storage unit 240, computer-executable instructions such as timing unit 114 and a controller such as controller 260. Some embodiments may be provided in a computer program product that may include a non-transitory machine-readable medium, having stored thereon instructions, which may be used to program a computer, or other programmable devices, to perform methods as disclosed above. Having thus described exemplary embodiments of the invention, it will be apparent to those skilled in the art that modifications of the disclosed embodiments will be within the scope of the invention. Alternative embodiments may, accordingly, include more modules, fewer modules and/or functionally equivalent modules. The present disclosure is relevant to various types of in-vivo devices (e.g., in-vivo devices with one or more imagers, in-vivo devices with no imagers at all, etc.), and to various types of receivers. Hence the scope of the claims that follow is not limited by the disclosure herein.

The invention claimed is:

1. A method for filtering an interference from a noisy localization signal sensed by an in-vivo device, comprising:
for an electromagnetic localization signal burst sensed by electromagnetic field sensors in an in-vivo device with an electromagnetic field interference, the signal burst comprising n electromagnetic localization signals, each electromagnetic localization signal having a time duration $T_L$, performing for each electromagnetic localization signal,
cancelling out zero-order electromagnetic field interference and first-order electromagnetic field interference superimposed on the electromagnetic localization signal by, (i) outputting, by each electromagnetic field sensor, an alternating signal that represents the electromagnetic localization signal;
(ii) sampling, using sampling specifics, a first portion of the alternating signal during a first sampling window to obtain a first set of samples;
(iii) sampling, using the sampling specifics, a second portion of the alternating signal during a second sampling window to obtain a second set of samples; and
(iii) calculating a number ($N_R$) from the first and second sets of samples, $N_R$ representing the electromagnetic localization signal.

2. The method as in claim 1, wherein the electromagnetic field interference comprises aperiodic and periodic electromagnetic field interferences of a zero-order, first-order, . . . , $n^{th}$-order, the interference signal comprising a fundamental frequency $f_I$ satisfying the condition $2T_I<T_L$, where $T_I=1/f_I$, the method further comprising:
(i) calculating a first number, Np, by adding up the first set of sample values;
(ii) calculating a second number, Nn, by adding up the second set of sample values;
(iii) calculating the number $N_R$ by subtracting the second number Nn from the first number Np; and
(iv) repeating steps (i) through (iii) for every electromagnetic localization signal in the localization signal burst.

3. The method as in claim 2, further comprising sampling the interference during one or more quiet periods in the localization signal burst and modifying $N_R$ based on the sampling results.

4. The method as in claim 3, wherein sampling the interference during a quiet period comprises:
sampling the interference during a third sampling window and a forth sampling window to respectively obtain a third set of samples and a fourth set of samples;
calculating a third number by adding up the samples of the third set of samples, and a fourth number by adding up the samples of the fourth set of samples; and
calculating a number NI1 from the third and forth numbers, the number NI1 representing the interference signal during the quiet period.

5. The method as in claim 4, further comprising modifying $N_R$ based on the number NI1.

6. The method as in claim 5, wherein modifying $N_R$ comprises calculating a number that represents the interference during each quiet period, extrapolating from the numbers representing the interference during the quiet periods a number that represents an expected interference during a time period when a localization signal is sensed.

7. The method as in claim 2, comprising adjusting the sampling specifics to accommodate for changes in the fundamental frequency $f_I$.

8. The method as in claim 7, wherein the adjusting sampling specifics is based on calculation of the fundamental frequency $f_I$ and phase of the interference signal.

9. The method as in claim 7, comprising calculating the fundamental frequency $f_I$ and phase of the interference signal during an interference learning period.

10. The method as in claim 1, wherein the samples of the second set of samples are respectively in phase with the samples of the first set of samples.

11. A system for filtering interferences superimposed on a localization signal sensed by an in-vivo device, the system comprising:
electromagnetic field sensors, to sense an electromagnetic localization signal burst on which an electromagnetic field interference is superimposed, the signal burst comprising n electromagnetic localization signals and one or more quiet periods, each electromagnetic localization signal having a time duration $T_L$, the electromagnetic field sensors to respectively output alternating signals in response to the sensed electromagnetic localization signals;

a controller configured to, for each alternating signal,
(i) sample, using sampling specifics, a positive portion of the alternating signal during a positive sampling window to obtain a first set of samples;
(ii) sample, using the sampling specifics, a negative portion of the alternating signal during a negative sampling window having the same duration as the positive sampling window, to obtain a second set of samples; and
(iii) calculate a number $N_R$ from the first and second sets of samples, that approximately represents the alternating signal, to thereby cancel out a zero-order electromagnetic field interference and a first-order electromagnetic field interference superimposed on the alternating signal.

12. The system as in claim 11, wherein the electromagnetic field interference comprises aperiodic and periodic electromagnetic field interferences of a zero-order, first-order, . . . , $n^{th}$-order, the interference signal comprising a fundamental frequency $f_I$ satisfying the condition $2T_I < T_L$, where $T_I = 1/f_I$, and wherein the controller is further configured to,
(i) calculate a first number, Np, by adding up values of the first set of samples;
(ii) calculate a second number, Nn, by adding up values of the second set of samples;
(iii) calculate the number $N_R$ by subtracting the second number Nn from the first number Np, the number $N_R$ representing a localization signal corresponding to the pertinent alternating signal; and
(iv) repeat operations (i) through (iii) for every other alternating signal in the localization signal burst.

13. The system as in claim 12, wherein the controller is further configured to sample an interference signal during one or more quiet periods in the localization signal burst, to calculate a fiducial number that represents the interference in each quiet period, to extrapolate, from the fiducial numbers, a number $N_Q$ representative of the interference during the localization signal, and to modify $N_R$ based on the extrapolated number $N_Q$.

14. The system as in claim 13, wherein the controller is configured to modify $N_R$ by subtracting $N_Q$ from $N_R$.

15. The system as in claim 12, wherein the controller is configured to adjust sampling specifics to accommodate for changes in the fundamental frequency $f_I$.

16. The system as in claim 15, wherein the controller is configured to adjust sampling specifics based on calculation of the fundamental frequency $f_I$ and phase of the interference signal.

17. The system as in claim 16, wherein the controller is configured to calculate the fundamental frequency $f_I$ and phase of the interference signal during an interference learning period.

18. The system as in claim 11, wherein the samples of the second set of samples are respectively in phase with the samples of the first set of samples.

19. A method comprising:
for an electromagnetic localization signal burst sensed in an in-vivo device, the signal burst comprising n electromagnetic localization signals, performing for each electromagnetic localization signal:
outputting, by each of a plurality of electromagnetic field sensors, an alternating signal that represents the electromagnetic localization signal;
sampling a first portion of the alternating signal during a first sampling period to obtain a first set of samples;
sampling a second portion of the alternating signal during a second sampling period to obtain a second set of samples; and
calculating a number from the first and second sets of samples, the number representing the electromagnetic localization signal.

* * * * *